United States Patent
Garrido

(10) Patent No.: US 10,342,722 B2
(45) Date of Patent: Jul. 9, 2019

(54) SURGICAL TABLES FOR SPINAL SURGERIES EMPLOYING LORDOSIS ADJUSTMENT SUBASSEMBLIES ROTATABLY CONNECTED TO RIGID FRAMES, AND RELATED SYSTEMS AND METHODS

(71) Applicant: Benito J. Garrido, Cornelius, NC (US)

(72) Inventor: Benito J. Garrido, Cornelius, NC (US)

( * ) Notice: Subject to any disclaimer, the term of this patent is extended or adjusted under 35 U.S.C. 154(b) by 0 days.

(21) Appl. No.: 15/387,652

(22) Filed: Dec. 22, 2016

(65) Prior Publication Data

US 2018/0177658 A1 Jun. 28, 2018

(51) Int. Cl.
| | |
|---|---|
| *A61B 17/70* | (2006.01) |
| *A61G 13/00* | (2006.01) |
| *A61G 13/12* | (2006.01) |
| *A61G 13/04* | (2006.01) |

(52) U.S. Cl.
CPC ...... *A61G 13/0054* (2016.11); *A61G 13/1245* (2013.01); *A61B 17/7083* (2013.01); *A61G 13/04* (2013.01)

(58) Field of Classification Search
CPC .. A61G 7/075; A61G 7/0755; A61G 13/1205; A61G 13/1245; A61G 13/0054
See application file for complete search history.

(56) References Cited

U.S. PATENT DOCUMENTS

| | | |
|---|---|---|
| 5,088,706 A | 2/1992 | Jackson |
| 5,131,106 A | 7/1992 | Jackson |
| 5,444,882 A | 8/1995 | Andrews et al. |
| 5,613,254 A | 3/1997 | Clayton et al. |
| 6,076,525 A * | 6/2000 | Hoffman ........ A61G 13/12 128/845 |
| 6,260,220 B1 | 7/2001 | Lamb et al. |
| 7,600,281 B2 | 10/2009 | Skripps |
| 7,669,262 B2 | 3/2010 | Skripps et al. |
| 8,060,960 B2 | 11/2011 | Jackson |

(Continued)

OTHER PUBLICATIONS

"Modular Table System" six-page brochure by Mizuho Osi downloaded on or before Mar. 7, 2016 from http://www.eastwindsurgical.com/wp-content/uploads/2015/04/Axis-Jackson-Brochure-2-08-3.pdf.

*Primary Examiner* — Lynnsy M Summitt
*Assistant Examiner* — Tara Rose E Carter
(74) *Attorney, Agent, or Firm* — Stephen R. Bylciw, Esq.

(57) ABSTRACT

Surgical tables employing lordosis adjustment subassemblies connected by hinge portions to rigid support frames, and related systems and methods are disclosed. A surgical table includes a frame supporting a patient in a prone position through subassemblies including body and leg pads. Relative positions of the pads determine a lumbar sagittal lordosis for the patient, and movements of the frame may disrupt a sterile field during surgery and increase opportunities for infections. By rotatably coupling the leg pad as part of a lordosis adjustment subassembly to the frame, a distal end of the leg pad may pass through an inner space defined by the frame to change the relative position of the pads according to the surgical procedures performed while minimizing frame movement. In this manner, post-operative long-term patient outcomes may be improved by providing optimal degrees of lordosis for the surgical procedures occurring during a surgical visit while minimizing infections.

18 Claims, 14 Drawing Sheets

(56) References Cited

U.S. PATENT DOCUMENTS

| | | | |
|---|---|---|---|
| 2006/0138743 A1* | 6/2006 | Beal | B62K 25/04 280/275 |
| 2006/0253985 A1 | 11/2006 | Skripps | |
| 2006/0260515 A1* | 11/2006 | Hodges | A47B 37/00 108/6 |
| 2010/0275376 A1* | 11/2010 | Benzo | A61G 7/015 5/618 |
| 2013/0312188 A1* | 11/2013 | Jackson | A61G 7/015 5/618 |

* cited by examiner

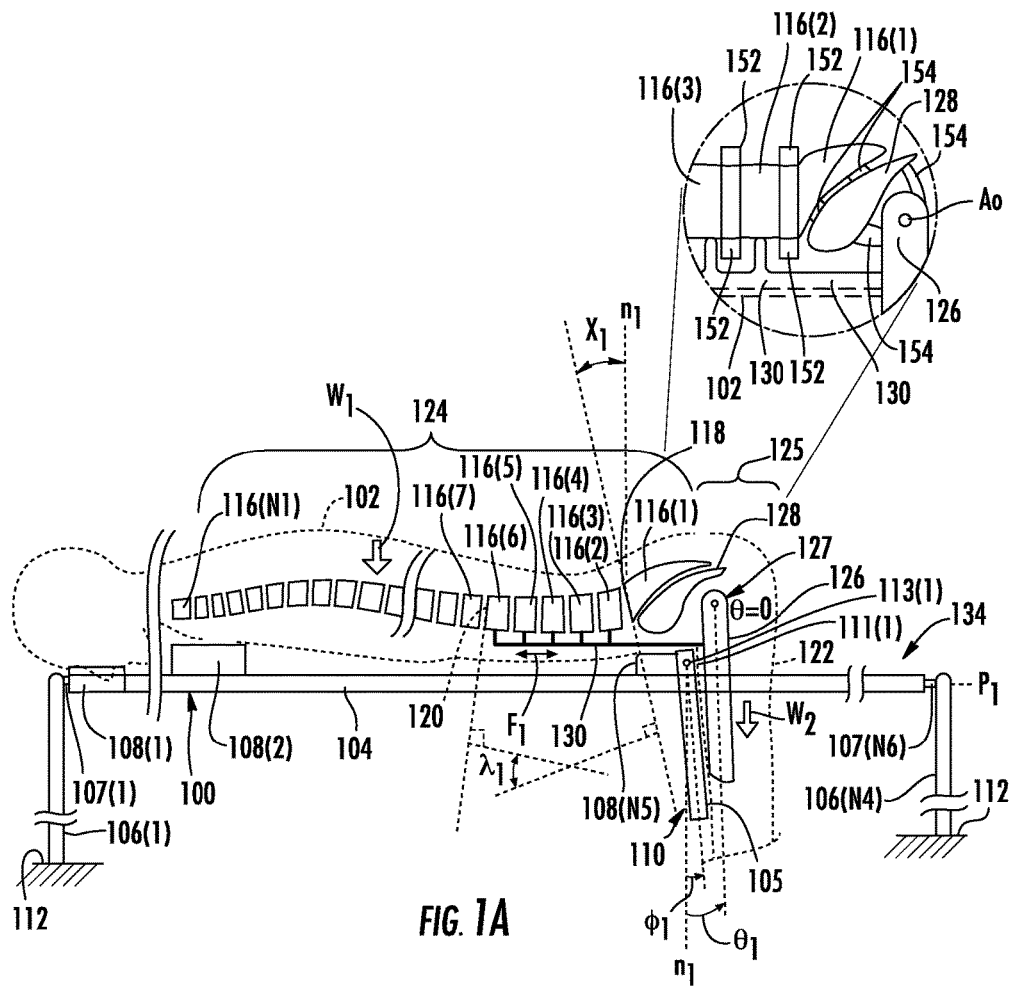
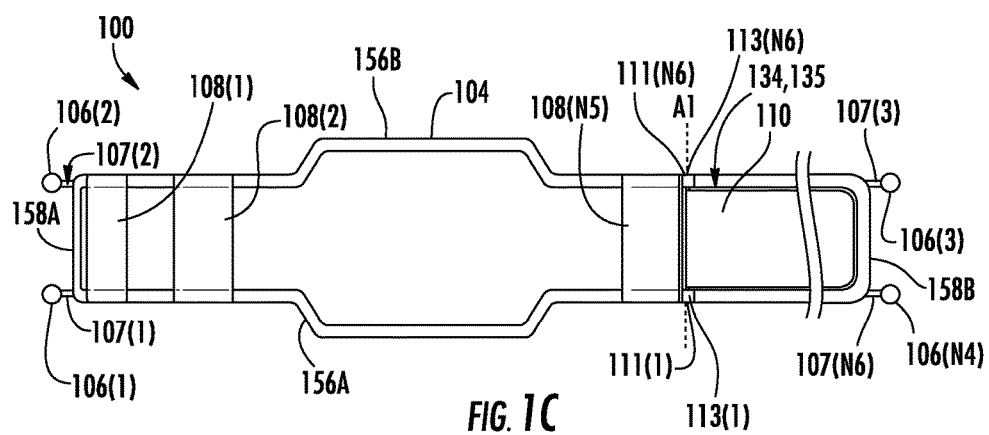
FIG. 1A
FIG. 1C

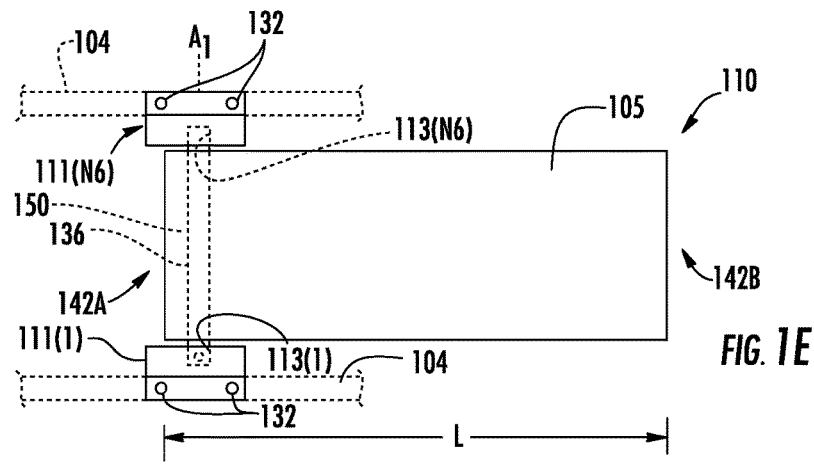
FIG. 1E
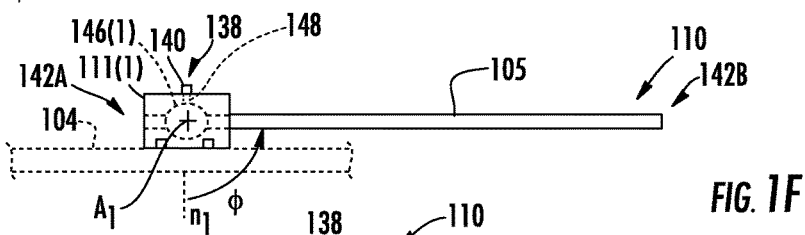
FIG. 1F
FIG. 1G
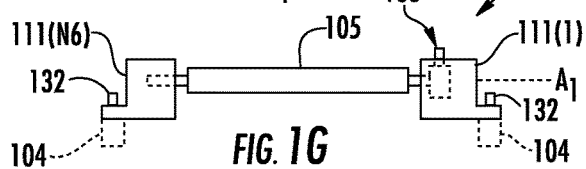
FIG. 1H
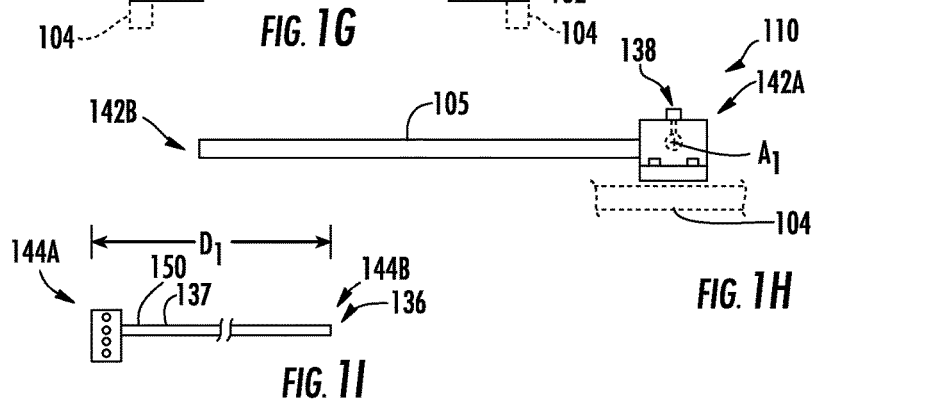
FIG. 1I
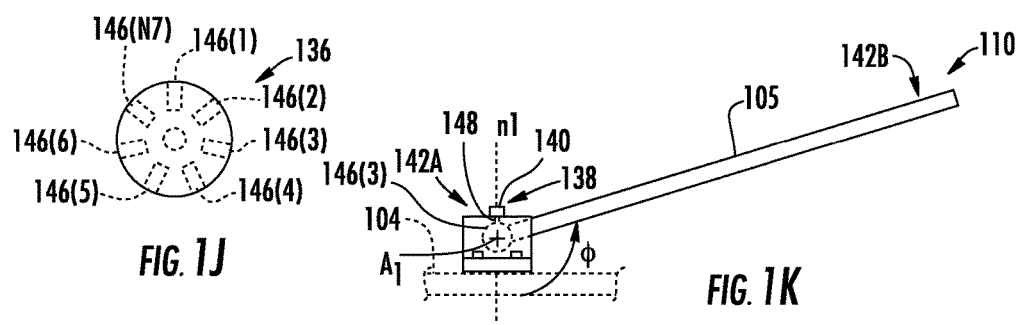
FIG. 1J
FIG. 1K

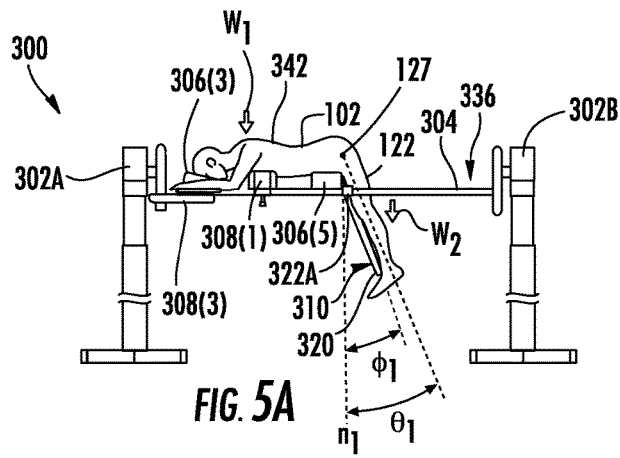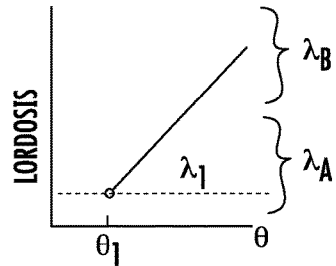
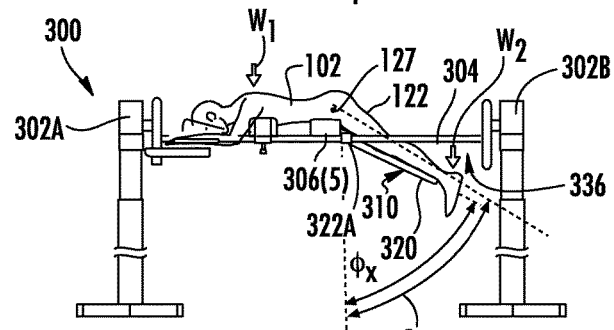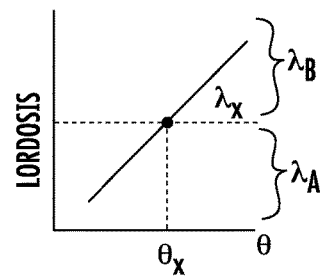
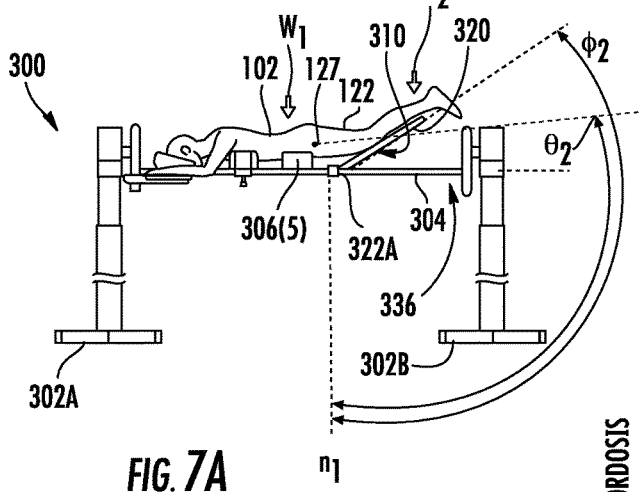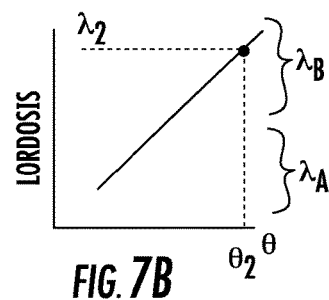

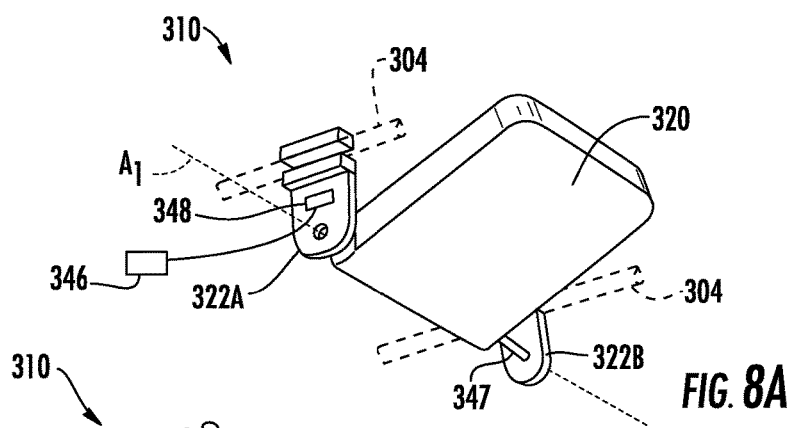
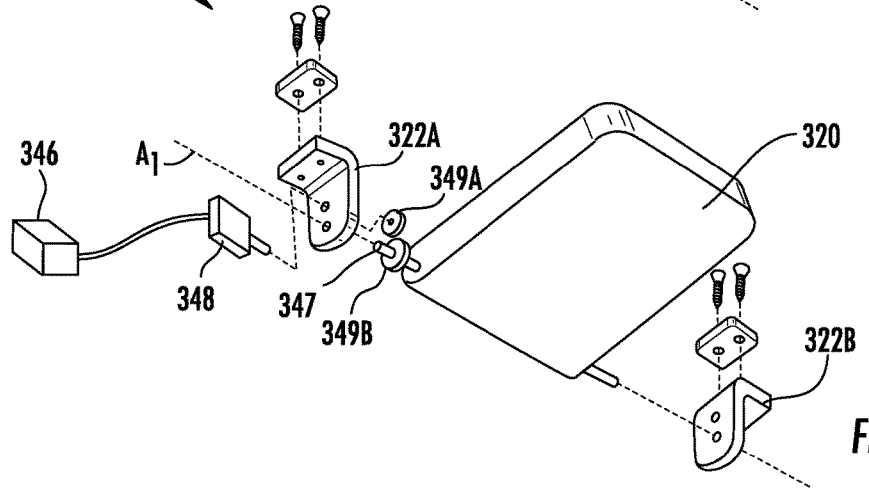
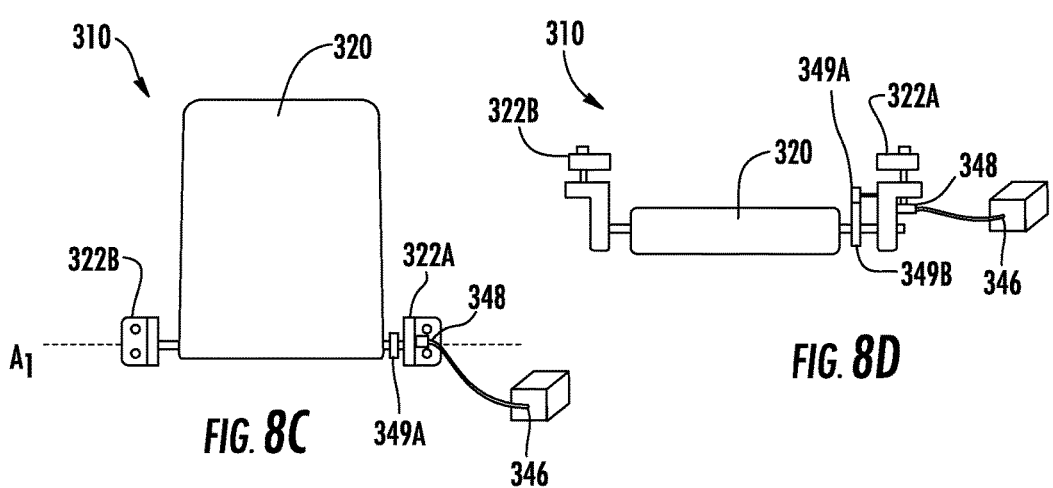

US 10,342,722 B2

SURGICAL TABLES FOR SPINAL SURGERIES EMPLOYING LORDOSIS ADJUSTMENT SUBASSEMBLIES ROTATABLY CONNECTED TO RIGID FRAMES, AND RELATED SYSTEMS AND METHODS

BACKGROUND

Field of the Disclosure

The technology of the disclosure relates to patient support devices and related assemblies and methods for positioning patients during spinal surgery.

Technical Background

A vertebral column of a patient extends from the skull to the pelvis and provides support and protection to the patient. The column includes vertebrae separated by fibrocartilage structures (intervertebral disks) for shock absorption. A spinal cord of the patient is protected by being disposed within the vertebral canal that is formed by openings through the vertebrae and the column serves as a protective enclosure for the spinal cord from which branching nerves extend therefrom. The branching nerves and the spinal cord together are part of a central nervous system enabling communication between the brain and other body parts of the patient. The column also helps support the body of the patient, wherein vertebrae are positioned by a set of ligaments, muscles and tendons interconnecting the vertebrae and enabling relative movement between adjacent vertebrae. However, medical intervention may be necessary when abnormalities occur at one or more locations of the column making relative movement at these locations problematic. Exemplary abnormalities necessitating medical intervention include degenerative disc disease, spondylolisthesis, trauma, deformities, tumors, stenosis, and pseudoarthrosis (failed spine fusion surgery). Medical intervention may involve preventing relative movement at these problematic locations using spine fusion surgery. Pain may be lessened and healing may occur after preventing this relative movement.

Conventional spine fusion surgery involves supporting the patient on a surgical table within a sterile field. The patient may be positioned in a prone position with a reduced lumbar lordosis sagittal profile ("reduced lordosis profile") that allows posterior access by the attending surgeon to the vertebrae. The sterile field may be optimally maintained by minimizing movement of both the table and sterile drapes during surgery when various combinations of pedicle screws, interbody devices, and/or connecting rods may fix adjacent vertebrae relative to each other. Upon patient recovery, the lumbar vertebrae may remain fixed in this less-optimal reduced lordosis profile. In this case, a positive sagittal balance may result where the patient leans forward and adopts an undesirable "bent-knee, bent-waist" walking gait with associated pain and complications. Accordingly, new approaches are needed to adjust lordosis during surgery to avoid patient sterile field contamination and other surgical complications while enabling better long-term patient outcomes.

SUMMARY OF THE DETAILED DESCRIPTION

Embodiments disclosed herein include surgical tables employing lordosis adjustment subassemblies rotatably connected to rigid frames, and related systems and methods. A surgical table includes a frame supporting a patient in a prone position through subassemblies including body and leg pads. Relative positions of the pads determine a lumbar sagittal lordosis for the patient, and movements of the frame may disrupt a sterile field during surgery and increase opportunities for infections. By rotatably coupling the leg pad as part of a lordosis adjustment subassembly to the frame, a distal end of the leg pad may pass through an inner space defined by the frame to change the relative position of the pads according to the surgical procedures performed while minimizing frame movement. In this manner, post-operative long-term patient outcomes may be improved by providing optimal degrees of lordosis for the surgical procedures occurring during a surgical visit while minimizing infections.

In one embodiment, a surgical table for supporting a patient during spinal surgery is disclosed. The surgical table includes a rigid frame including first and second elongated portions spaced apart and connected by a plurality of traverse elements, wherein the first and the second elongated portions and the plurality of traverse elements define an inner space. The surgical table further includes at least one body pad connected to the rigid support frame and configured to transfer a weight of a portion of the patient to the rigid support frame during the spinal surgery, wherein the portion is superior to a hip joint of the patient. The surgical table further includes a lordosis adjustment subassembly including a leg pad and a hinge portion, wherein the leg pad is connected to the rigid frame with the hinge portion, the hinge portion defining a range of motion of a distal end of the leg pad through the inner space. In this manner, injuries from pedicle screw insertion may be avoided and patient long-term comfort improved.

In another embodiment, a lordosis adjustment subassembly for changing sagittal lumbar lordosis of a patient supported on a surgical table during spinal surgery is disclosed. The lordosis adjustment subassembly includes a leg pad configured to support at least one thigh of the patient when the patient is supported the prone position, wherein the leg pad extends from a proximate side of the leg pad to a distal side of the leg pad. The lordosis adjustment subassembly also includes an axle secured to the leg pad. The lordosis adjustment subassembly further includes a hinge portion configured to be secured to a rigid frame of a surgical table, wherein the hinge portion is coupled to the leg pad through the axle, wherein the axle defines an axis of rotation enabling the distal side of the leg pad to rotate about the hinge portion. In this manner, spinal surgeries can be most efficiently completed while avoiding injury to the patient.

In another embodiment, a method is disclosed for fusing vertebrae together during spinal surgery. This method may include pivoting, with a rigid frame of a surgical table positioned by a plurality of piers, a patient from a supine position to a prone position when the patient is supported by the rigid frame via at least one body pad connected to the rigid support frame and a lordosis adjustment subassembly coupled to the rigid frame. The method may further include creating, with the lordosis adjustment subassembly of the surgical table, a first sagittal lumbar lordosis by rotating a leg pad of the lordosis adjustment subassembly to the first angular subassembly position with respect to the rigid frame. The method may further include upon creation of the first sagittal lumbar lordosis, inserting pedicle screws into the vertebrae. The method may further include creating, with the lordosis adjustment subassembly, a second sagittal lumbar lordosis by rotating the leg pad to the second angular subassembly position with respect to the rigid frame. The method may further include upon creation of the second sagittal lumbar lordosis, fusing the vertebrae together by attaching the pedicle screws together with the immobilization rod. In this manner, vertebrae may be fused together to facilitate a patient posture consistent with long-term comfort and pedicle screw insertions may occur while avoiding patient injury.

Additional features and advantages will be set forth in the detailed description which follows, and in part will be readily apparent to those skilled in the art from that description or recognized by practicing the embodiments as described herein, including the detailed description that follows, the claims, as well as the appended drawings.

It is to be understood that both the foregoing general description and the following detailed description present embodiments, and are intended to provide an overview or framework for understanding the nature and character of the disclosure. The accompanying drawings are included to provide a further understanding, and are incorporated into and constitute a part of this specification. The drawings illustrate various embodiments, and together with the description serve to explain the principles and operation of the concepts disclosed.

BRIEF DESCRIPTION OF THE FIGURES

So that the manner in which the above recited features of the present disclosure can be understood in detail, a more particular description of the disclosure, briefly summarized above, may be had by reference to embodiments, some of which are illustrated in the appended drawings. It is to be noted, however, that the appended drawings illustrate only exemplary embodiments and are therefore not to be considered limiting of its scope, may admit to other equally effective embodiments.

FIGS. 1A and 1B are right lateral schematic views of a patient being supported on an exemplary surgical table in a prone position, wherein vertebrae of the patient are positioned with exemplary first and second sagittal lumbar lordosis angles with an exemplary lordosis adjustment subassembly, respectively;

FIGS. 1C and 1D are top and rear schematic views of the surgical table of FIG. 1B with the patient removed;

FIGS. 1E through 1H are, respectively, a top view, a right side view, a front view, and a left side view of the lordosis adjustment subassembly of FIG. 1A in an exemplary angular subassembly position;

FIGS. 1I and 1J are a rear view and a right side view of an axle of a locking system of the lordosis adjustment subassembly of FIG. 1E;

FIG. 1K is a right side view of the lordosis adjustment subassembly of FIG. 1E in an exemplary alternative angular subassembly position;

FIG. 5A is a right side view of the surgical table of FIG. 3A supporting the patient with a leg pad of the lordosis adjustment subassembly moved to an exemplary subassembly angular position with respect to the rigid frame resulting in at least one thigh of the patient to be positioned at an exemplary angular thigh position relative to a superior body portion of the patient and the rigid frame;

FIG. 5B is a graph showing the relationship of the angular thigh position of FIG. 5A to a respective lumbar lordosis angle;

FIG. 6A is a right side view of the surgical table of FIG. 5A supporting the patient with the leg pad moved to an exemplary secondary subassembly angular position with respect to the rigid frame resulting in the at least one thigh to be positioned at an exemplary secondary angular thigh position relative to the superior body portion of the patient and the rigid frame;

FIG. 6B is a graph showing the relationship of the secondary angular thigh position of FIG. 6A to a respective second lumbar lordosis angle;

FIG. 7A is a right side view of the surgical table of FIG. 5A supporting the patient with the leg pad moved to an exemplary tertiary subassembly angular position with respect to the rigid frame resulting in the at least one thigh to be positioned at an exemplary tertiary angular thigh position relative to the superior body portion of the patient and the rigid frame;

FIG. 7B is a graph showing the relationship of the tertiary angular thigh position of FIG. 7A to a respective third lumbar lordosis angle;

FIGS. 8A through 8D are a bottom perspective view, bottom perspective exploded view, top view, and front view, respectively, of the lordosis adjustment subassembly of FIG. 3A;

To facilitate understanding, identical reference numerals have been used, where possible, to designate identical elements that are common to the figures. It is contemplated that elements and features of one embodiment may be beneficially incorporated in other embodiments without further recitation.

DETAILED DESCRIPTION

Reference will now be made in detail to the embodiments, examples of which are illustrated in the accompanying drawings, in which some, but not all embodiments are shown. Indeed, the concepts may be embodied in many different forms and should not be construed as limiting herein; rather, these embodiments are provided so that this disclosure will satisfy applicable legal requirements. Whenever possible, like reference numbers will be used to refer to like components or parts.

Embodiments disclosed herein include surgical tables employing lordosis adjustment subassemblies rotatably connected to rigid frames, and related systems and methods. A surgical table includes a frame supporting a patient in a prone position through subassemblies including body and leg pads. Relative positions of the pads determine a lumbar sagittal lordosis for the patient, and movements of the frame may disrupt a sterile field during surgery and increase opportunities for infections. By rotatably coupling the leg pad as part of a lordosis adjustment subassembly to the frame, a distal end of the leg pad may pass through an inner space defined by the frame to change the relative position of the pads according to the surgical procedures performed while minimizing frame movement. In this manner, post-operative long-term patient outcomes may be improved by providing optimal degrees of lordosis for the surgical procedures occurring during a surgical visit while minimizing infections.

Figure 1B:
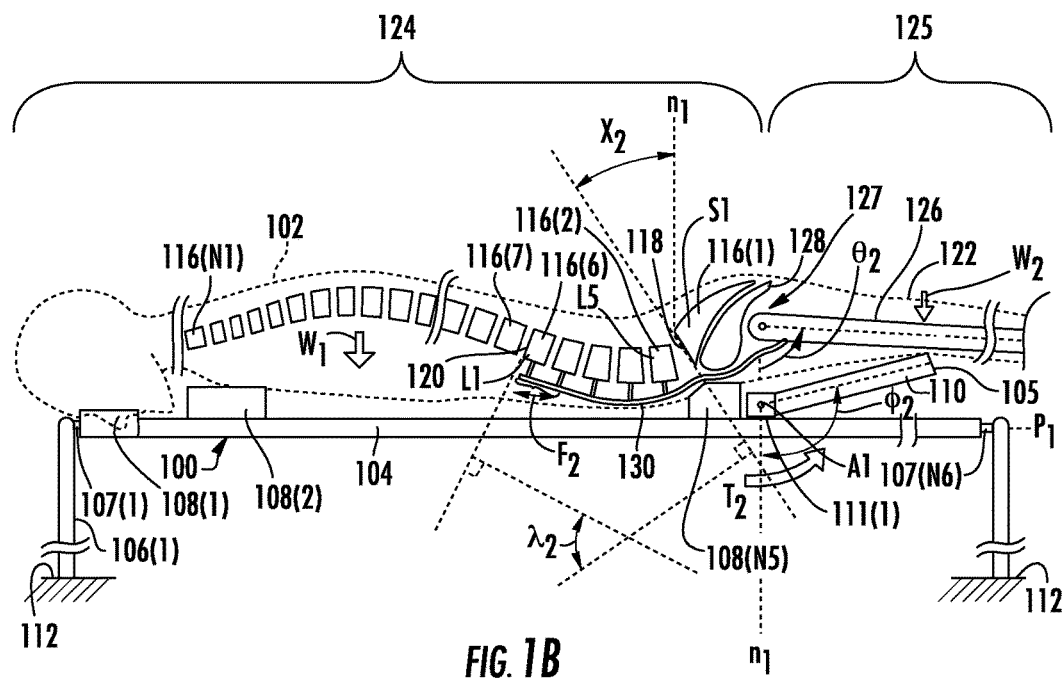
Figure 1D:
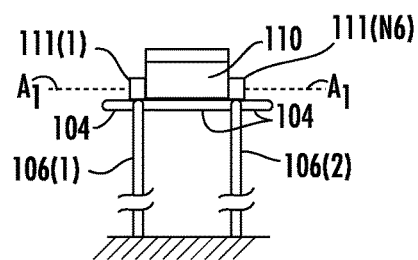

In this regard, FIGS. 1A and 1B are right lateral schematic views of a patient 102 being supported on an exemplary surgical table 100 in a prone position, wherein vertebrae 116(1)-116(6) of the patient 102 are positioned with an exemplary first sagittal lumbar lordosis angle $\lambda 1$ and an exemplary second sagittal lumbar lordosis angle $\lambda 2$, respectively. FIGS. 1C and 1D are top and rear schematic views of the surgical table 100 of FIG. 1B with the patient 102 removed The surgical table 100 includes a rigid frame 104, a plurality of piers 106(1)-106(N4), at least one body pad 108(1)-108(N5), and a lordosis adjustment subassembly 110.

The rigid frame 104 is a structural member of the surgical table 100 providing a foundation to secure the body pads 108(1)-108(N2) and the lordosis adjustment assembly 110 which transfer a weight of the patient 102 to the rigid frame 104. The rigid frame 104 may also be used as a foundation to secure diagnostic equipment (not shown) during surgery. The rigid frame 104 may be made of strong materials, for example, metal, aluminum, or composites to statically support the weight of the patient 102 during surgery. The rigid frame 104 includes elongated portions 156A, 156B and transverse elements 158A, 158B that may be disposed in or substantially in a geometric plane P1. The elongated portions 156A, 156B and transverse elements 158A, 158B are connected and arranged to define an inner space 134. The inner space 134 is configured to allow movement of a distal end of a leg pad (discussed later) of the lordosis adjustment subassembly 110 to pass through in order to control sagittal lumbar lordosis of the patient 102 as desired during surgery. The inner space 134 may include a closed polygonal shape 135 to accommodate a shape of the patient 102 when the patient 102 is in a prone position while reducing a footprint of the surgical table 100. In this manner, the rigid frame 104 may support the patient 102.

The piers 106(1)-106(N4) support and position the rigid frame 104 relative to a surgical floor 112. The surgical table 100 may also include frame receiving interfaces 107(1)-107(N6) to enable coupling of the rigid frame 104 to the piers 106(1)-106(N4). In a non-limiting example, the frame receiving interfaces 107(1)-107(N6) may include, for example, fasteners to couple the rigid frame 104 to the piers 106(1)-106(N4). In other non-limiting examples, the frame receiving interfaces 107(1)-107(N6) may also include bearing mechanisms (FIGS. 10A, 10B) to allow the rigid frame 104 to move relative to the piers 106(1)-106(N4). The body pads 108(1)-108(N5) may be coupled to the rigid frame 104 and transfer at least a fractional weight W1 of a portion 124 of the patient 102 to the rigid frame 104. The fractional weight W1 may originate from at least a portion 124 of the patient 102 superior to the hip joint 127. Another fractional weight W2 of the patient 102 may originate from the thighs 122 of the patient 102. This fractional weight W2 may be transferred to the rigid frame 104 through a leg pad 105 of the lordosis adjustment subassembly 110. The entire weight of the patient may be the sum of the fractional weights W1, W2. In this manner, the weight of the patient 102 may be supported by the surgical table 100.

In order to transfer the fractional weight W2 to the rigid frame 104, the leg pad 105 is rotatably coupled to the rigid frame 104 with at least one hinge portion 111(1)-111(N6) of the lordosis adjustment subassembly 110, an axle 136 of the lordosis adjustment subassembly 110, and a locking system 138. When the locking system 138 is engaged, the fractional weight W2 may be transferred from the leg pad 105 to the rigid frame 104 via the axle 136 and the at least one hinge system 111(1)-111(N6). Another consequence of having the locking system 138 engaged is that a relative position between the body pads 108(1)-108(N5) and the leg pad 105 is set. Accordingly as the portion 124 of the patient 102 superior of the hip joint 127 is supported by the body pads 108(1)-108(N5) that are coupled to the rigid frame 104 and the thighs 122 are supported by the leg pad 105, then the thighs 122 are positioned at an angular subassembly position 1 (phi) relative to the rigid frame 104. In this manner, the patient 102 may be supported with the angular subassembly position Φ (phi) to facilitate (as discussed later) a desired sagittal lumbar lordosis angle during surgery.

This angular subassembly position Φ (phi) of the patient 102 may be adjusted. The hinge portions 111(1)-111(N6) may include bearings 113(1)-113(N6) in communication with the axle 136 of the lordosis adjustment subassembly 110. The axle 136 may be coupled to the leg pad 105, for example, with an adhesive or fasteners (not shown), so that the axle 136 and the leg pad 105 may together rotate about the axis of rotation A1. In this way, the bearings 113(1)-113(N6) and the axle 136 establish an axis of rotation A1 for the leg pad 105. The leg pad 105 may be actuated directly manually or indirectly by mechanical, electrical, or hydraulic means (not shown) to rotate about the axis of rotation A1, so that the desired angular subassembly position 1 (phi) may be achieved relative to a normal n1 of the rigid frame 104.

Once the angular position Φ (phi) is achieved, the lordosis adjustment subassembly 110 may remain reversibly locked in that position. To this end, the lordosis adjustment subassembly 110 may further includes the locking system 138 to prevent angular movement of the leg pad 105 relative to the rigid frame 104 as desired once the angular subassembly position Φ (phi) is achieved. In one non-limiting embodiment, the locking system 138 may create a mechanical interference or frictional force between at least one of the hinge portions 111(1)-111(N6) and the axle 136 to apply a locking torque T2 to the leg pad 105 preventing angular movement of the leg pad 105 in response to the fractional weight W2. In this manner, the fractional weight W2 of the patient 102 may be supported by the surgical table 100.

The lordosis adjustment subassembly 110 may include the hinge portions 111(1)-111(N6), the axle 136, the locking system 138, and the leg pad 105. Each of these are now be discussed sequentially. The leg pad 105 facilitates a transfer of the fractional weight W2 to the rigid frame 105. The proximate side 142A of the leg pad 105 is generally positioned to be near the hip joint 127, so that as the leg pad 105 supports the thighs 122 of the patient 102. The relative position of the leg pad 105 represented by the angular subassembly position Φ (phi) relative to the rigid frame 104 may determine an angular thigh position θ (theta) position of the patient 102, which as discussed later, may be used by the attending surgeon to control the sagittal lumbar lordosis of the patient 102.

With continued reference to FIGS. 1E through 1H, other details of the leg pad 105 are now provided. The leg pad 105 extends longitudinally along a length L from a proximate side 142A to a distal side 142B opposite of the proximate side 142A. The length L may be configured to be at least as long as a femur of the patient 102 to advantageously receive the fractional weight W2 through the knees of the patient 105. The length L may be, for example, in a range from twenty-four (24) inches to forty-eight (48) inches. The leg pad 105 may be configured to be coupled to the axle 136 at or near the proximate side 142A to minimize interference with the body pads 108(1)-108(N5) and enable the angle of rotation A1 to be located near the body pad 108(N5) supporting the hip joint 127. The length L and the shape of the leg pad 105 relative to the axis of rotation A1 may be configured to enable the leg pad 105 to pass through the inner space 134 of the rigid frame 104, so that the range of motion of the leg pad 105 about the axis of rotation A1 is maximized to provide the attending surgeon with a wide range of sagittal lumbar lordosis possibilities for the patient 102. The leg pad 105 may include, for example, one or more materials to minimize bruising to the patient 102 and to maintain the angular subassembly position Φ (phi) without collapsing under the application of the fractional weight W2.

The hinge portions 111(1), 111(N6) may be coupled to the rigid frame 104, for example with fasteners 132, or in other embodiments made integral with the rigid frame 104. The hinge portions 111(1)-111(N6) include the bearings 113(1), 113(N6) to communicate with the axle 136 attached to the leg pad 105, so that the leg pad 105 may rotate about the axis of rotation A1 and though an inner space 134 surrounded by the rigid frame 104. Rotation as discussed earlier may be provided, for example, with manual or powered means. In one embodiment, the locking system 138 may include a fastener 140 to couple with at least one of the hinge portions 111(1)-111(N6) and the axle 136 to create a mechanical interference with the axle 136 and at least one of the hinge portions 111(1)-111(N6), and thereby preventing rotation of the axle 136 relative to the hinge portions 111(1)-111(N6). The rigid frame 104 may fully support the fractional weight W2 through the axle 136. In this manner, the thighs 122 of the patient 102 may be supported and positioned to achieve the desired angular thigh position θ (theta) position to achieve the desired sagittal lumbar lordosis for the patient 102.

FIGS. 1I and 1J are a rear view and a right side view of the axle 136 of the lordosis adjustment subassembly of FIG. 1E. The axle 136 may be attached at the proximate side 142A of the leg pad 105 and in communication with the bearings 113(1)-113(N6) of the hinge portions 111(1)-111(N6). The axle 136 may include an elongated body 137 extending from a first side 144A to a second side 144B along a distance D1, wherein D1 may be in a range from eighteen (18) inches to forty-two (42) inches to traverse a lateral pelvis region of a patient 102. At least one connection surface 150 between the first side 144A and the second side 144B of the axle 136 may be coupled (e.g., adhesives, fasteners, etc.) to the leg pad 105 to provide co-rotation of the leg pad 105 and the axle 136 about the axis of rotation A1. The first side 144A and the second side 144B of the axle 136 may couple with the hinge portions 111(1), 111(N6). The first side 144A of the axle 136 may include inner surfaces 146(1)-146(N7) configured to couple with the locking system 138. In one non-limiting embodiment, the locking system 138 may include a cotter pin 140 configured to be received by one or more of the inner surfaces 146(1)-146(N7) of the axle 136. The hinge portion 111(1) may include an inner surface 148 forming a passageway for the cotter pin 140. In this arrangement, the cotter pin 140 may be configured to be received by the inner surface 148 of the hinge portion 111(1) and one of the inner surfaces 146(1)-146(N7) to form a mechanical interference to prevent rotation of the axle 136 and the leg pad 105 with respect to the rigid frame 104 and the hinge portion 111(1). The cotter pin 140 may be removed, for example manually, by the attending surgeon from the axle 136 and the hinge portion 111(1). When removed, the leg pad 115 may be adjusted, for example manually or with an actuator, to a different one of the angular subassembly position Φ (phi) before the cotter pin 140 may be inserted again into the hinge portion 111(1) and received within a different one of the inner surfaces 146(1)-146(N7). For example, FIG. IF illustrates the leg pad 105 locked at an angular subassembly position Φ (phi) with the cotter pin 140 engaged with (or received within) the inner surface 146(1). In contrast, FIG. 1K is a right side view of the leg pad 105 of the lordosis adjustment subassembly 110 of FIG. 1E in an exemplary alternative angular subassembly position. In this alternative angular subassembly position, the cotter pin 140 may be inserted instead into the the inner surface 146(3) to lock the leg pad 105 at the alternative angular subassembly position. When locked, the mechanical interference created by the cotter pin 140 engaging with the hinge portion 111(1) and at least one the inner surfaces 146(1)-146(N7) may lock the leg pad 105 in an angular subassembly position Φ (phi) and support the fractional weight W2 of the patient 102 as required to support the patient 102 during surgery. In this manner, the locking system 138 may be used to secure the leg pad 105 at different angular subassembly positions Φ (phi).

The angular subassembly position Φ (phi) of the lordosis adjustment subassembly 110 may be used to increase or decrease a sagittal lumbar lordosis angle λ of the vertebrae 116(1)-116(N1). Many approaches may be used to measure and quantify an angle (or amount of) sagittal lumbar lordosis, including the lordosis angle λ (lambda) discussed herein. With reference back to FIG. 1A, the sagittal lumbar lordosis angle λ may be measured as the angle λ (lambda) between a superior endplate 118 of a first sacral vertebra (S1) and a superior endplate 120 of a first lumbar vertebra (L1), wherein the first sacral vertebra (S1) and the first lumbar vertebra (L1) are illustrated respectively as vertebrae 116(1), 116(6). Accordingly, larger values of the lordosis angle λ are associated with greater values of sagittal lumbar lordosis. A normal range of the sagittal lumbar lordosis angle λ (lambda) associated with the vertebrae 116(1)-116(N1) may be dependent upon many factors including, gender, age, and body mass index. In one example, an exemplary normal range of the angle sagittal lumbar lordosis λ (lambda) may be from twenty (20) degrees to forty-five (45) degrees. It is noted that alternative measures of sagittal lumbar lordosis are also available, for example, a radius of curvature measurement based on locations of multiple vertebrae, wherein a smaller value of the radius of curvature is related to greater lordosis. As used herein, sagittal lumbar lordosis will be measured in terms of the angle λ (lambda) as illustrated in FIGS. 1A and 1B, but it is contemplated that other measures of quantifying lordosis may be used consistent with this disclosure. In this manner, the sagittal lumbar lordosis may be measured and quantified.

With reference back to FIGS. 1A and 1B, an angular thigh position θ (theta) of the thighs 122 of the patient 102 relative to a superior portion 124 of the patient 102 may be modified by changing the angular subassembly position Φ (phi) of the lordosis adjustment subassembly 110. The hinge portions 111(1)-111(N6) of the lordosis adjustment subassembly 110 may enable attending medical personnel to set the angular subassembly position Φ (phi) by manual or power-assisted actuator means. The lordosis adjustment subassembly 110 supports thighs 122 as part of the fractional weight W2 of the patient 102 while the body pads 108(1)-108(N5) support at least the fractional weight W1 of the patient 102. The fractional weight W2 may originate from the portion 125 of the patient 102 disposed inferior to the hip joint 127. A proximity between the body pads 108(1)-108(N5) and the rigid frame 104 may be independent of angular subassembly positions Φ (phi) of the leg pad 105 relative to the rigid frame 104. Accordingly, the angular thigh position θ (theta) of the thighs 122 of the patient 102 relative to the superior portion 124 of the patient 102 may move in response to rotation of the leg pad 105 relative to the rigid frame 104. In this manner, a desired angular thigh position θ may be achieved by changing the angular subassembly position Φ (phi).

With continuing reference to FIGS. 1A and 1B, the sagittal lumbar lordosis angle λ may be changed with the angular thigh position θ (theta). The femur bones 126 (FIG. 1A) of the thighs 122 are coupled to at least one of the vertebrae 116(1)-116(N1) through various internal structures, for example, ligaments 152, 154 interconnecting the femur bones 126, vertebrae 116(1)-116(N1), and the pelvis 128. In one illustrative example, the psoas muscle 130 of these internal structures connect various ones of the vertebra 116(1)-116(N1) to the femur bones 126. As is shown in FIG. 1A, the sagittal lumbar lordosis angle λ1 is relatively small (less spinal curvature) as the psoas muscle 130 is subject to a relatively low tensile force F1 as the femur bones 126 of the patient are positioned at a relatively small value of the angular thigh position θ1 (theta_1). In contrast, FIG. 1B illustrates that the femur bones 126 move in accordance with the changes of the angular thigh position θ (theta), and this movement increases tension in the psoas muscle 130 from force F1 to a greater force F2 that repositions various ones of the vertebrae 116(1)-116(N1) and increases lordosis from sagittal lumbar lordosis angle λ1 to sagittal lumbar lordosis angle λ2. It is also noted that as the femur bones 126 are angularly moved by the leg pad 105 to larger values of the angular thigh position θ (theta), that the pelvis inclination angle X may also increase from X1 to X2 because the femur bones and the pelvis are coupled with the various internal structures (e.g., ligaments) as discussed above. In an effort to illustrate this, FIGS. 1A and 1B illustrate a pelvis inclination angle X1 increasing to a pelvis inclination angle X2 relative to a normal vector n1 extending from the rigid frame 104 as the angular thigh position θ (theta) is increased. This increase to the pelvis inclination angle X2 may also facilitate an increase in lordosis from the sagittal lumbar lordosis angle λ1 to the sagittal lumbar lordosis angle λ2. Accordingly, the sagittal lumbar lordosis angle λ may be adjusted by use of the leg pad 105 to change the angular thigh position θ.

Figure 2A:
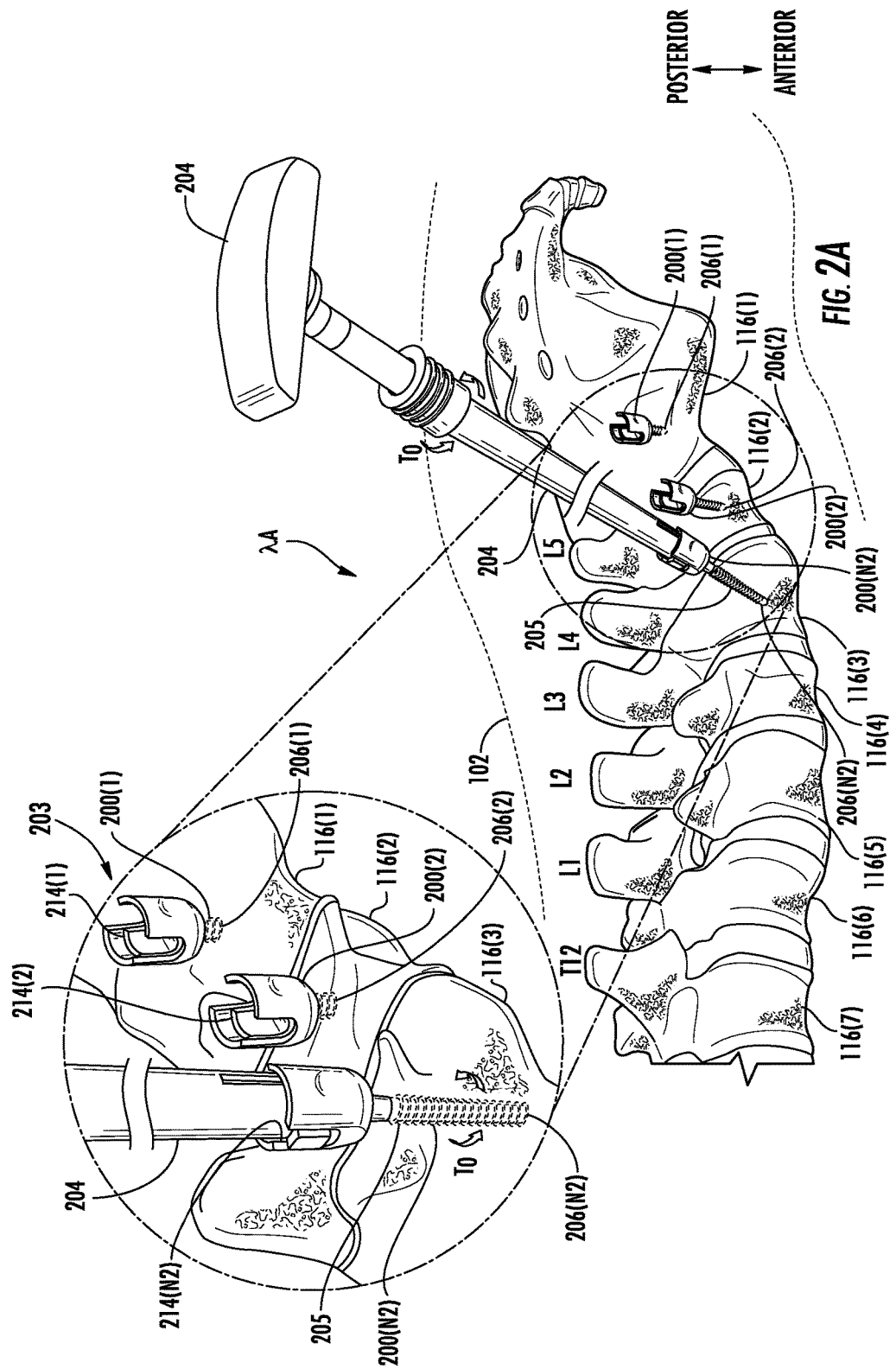
FIG. 2A is a posterior perspective partial view of an exemplary immobilization system being attached to vertebrae by inserting pedicle screws into the vertebrae while the vertebrae are positioned with the first sagittal lumbar lordosis angle.
Figure 2B:
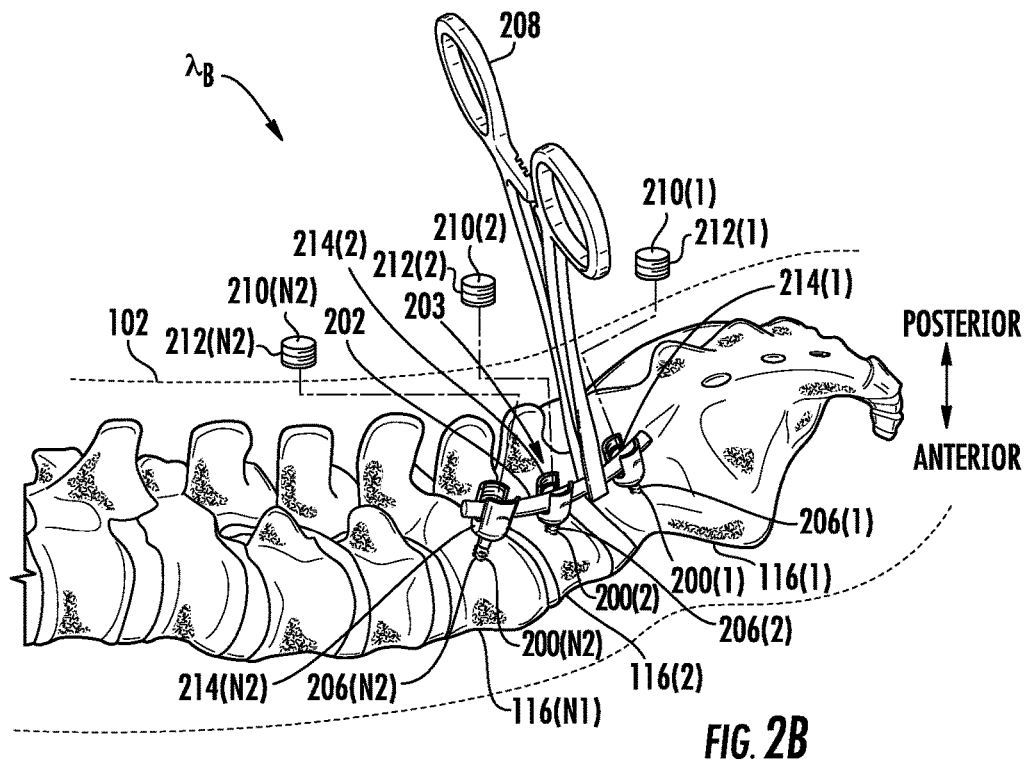
FIG. 2B is a posterior perspective partial view of the pedicle screws of the immobilization system of FIG. 2A being connected together with an exemplary immobilization rod while the vertebrae are positioned with the second sagittal lumbar lordosis angle.
Figure 2C:
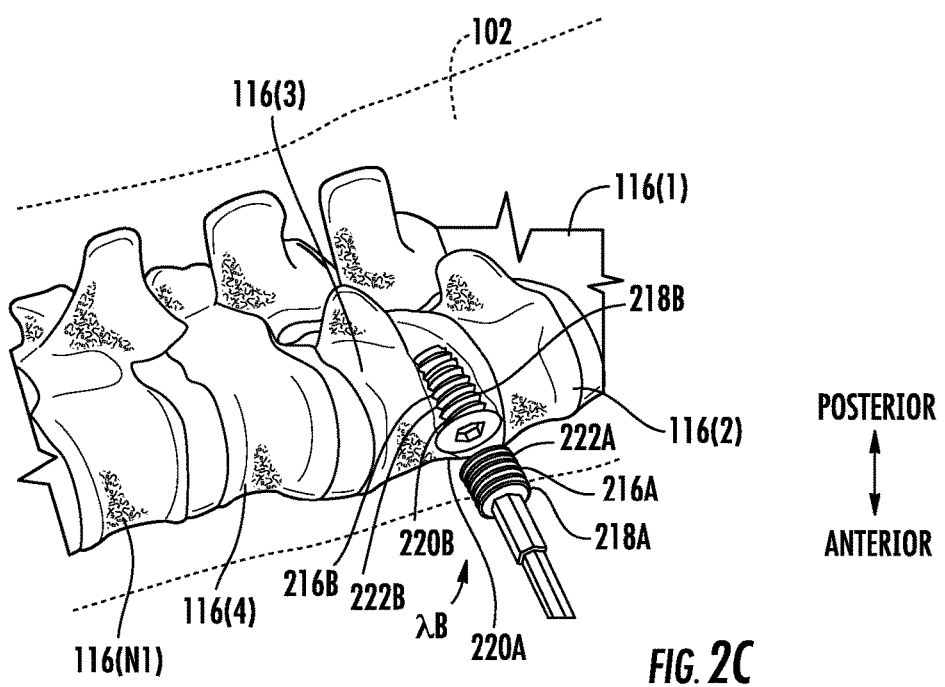
FIG. 2C is a partial lateral view of exemplary interbody cages being implanted between adjacent ones of the vertebrae of a patient in a prone position while the vertebrae are positioned with the second sagittal lumbar lordosis angle.

FIGS. 2A through 2C, illustrate several exemplary surgical procedures that may be performed upon vertebrae 116(1)-116(N1) of a patient 102 while utilizing the surgical table 100 employing the lordosis adjustment subassembly 100 rotatably connected to the rigid frame 104. These procedures may be performed more advantageously with optimal values of the sagittal lumbar lordosis angle λ to produce better long-term patient outcomes. Examples of these procedures are immobilization rod installation, pedicle screw insertion, and interbody cage implantation during spine fusion surgery when multiple vertebrae are immobilized relative to each other.

In this regard, FIGS. 2A and 2B illustrate posterior perspective partial views of pedicle screws 200(1)-200(N2) and an immobilization rod 202 of an immobilization system 203 (FIG. 2B) being attached to the vertebrae 116(1)-116(N1) of a patient 102, to immobilize (or "fuse") the vertebrae 116(1)-116(N1) relative to each other. The immobilization system 203 includes various components to be discussed below such as an immobilization rod 202, pedicle screws 200(1)-200(N2), and secondary fasteners 210(1)-210(N2). When completed, the immobilization system 203 may be used to immobilize (or "fuse") the vertebrae 116(1)-116(N1) of a patient 102 relative to each other. Immobilizing the vertebrate 116(1)-116(N1) with the immobilization system 203 is one medical approach to treat abnormalities that the patient 102 may experience, for example, degenerative disc disease, spondylolisthesis, trauma, deformities, tumors, stenosis, and pseudoarthrosis. The immobilization may offer one or more benefits for the patient 102 including pain reduction, improved healing, and structural support for an improved surgical outcome. Various quantities of the vertebrae 116(1)-116(N1) may be immobilized depending upon the needs of the patient 102 to provide optimal benefit to the patient 102.

The immobilization system 203 includes components that collectively form a rigid mechanical assembly, which when anchored to the vertebrae 116(1)-116(N1), cause the vertebrae 116(1)-116(N1) to be immobilized to each other. As shown in FIG. 2A, the immobilization system 203 includes the pedicle screws 200(1)-200(N2) being inserted into the vertebrae 116(1)-116(N1), for example, with a manual torque driver 204. In this regard, the manual torque driver 204 may interface with each of the pedicle screws 200(1)-200(N2) and apply a torque T0 to rigidly fix threads 205 of the pedicle screws 200(1)-200(N2) relative to the vertebrae 116(1)-116(N1) to form pedicle screw attachments 206(1)-206(N2) between the immobilization system 203 and the vertebrae 116(1)-116(N1). The pedicle screws 200(1)-200(N2) are preferably inserted when the vertebrae are positioned with the relatively low value of the first sagittal lumbar lordosis angle λA consistent with the sagittal lumbar lordosis λ1 illustrated in FIG. 1A.

With reference back to FIG. 1B, the immobilization rod 202 of the immobilization system 203 may be rigidly secured to the pedicle screws 200(1)-200(N2) and may be placed in abutment using placement means (e.g., forceps 208). Once the immobilization rod 202 is in abutment, the secondary fasteners 210(1)-210(N2) may rigidly secure the immobilization rod 202 to the pedicle screws 200(1)-200(N2), for example, by engaging male threads 212(1)-212(N2) of the secondary fasteners 210(1)-210(N) with female threads 214(1)-214(N2) of the pedicle screws 200(1)-200(N2). This engagement causes the immobilization rod 202 to be clamped securely to the pedicle screws 200(1)-200(N2) to form the rigid attachment. As discussed later, forming the rigid attachment is preferably done with a sagittal lumbar lordosis angle λ2 (FIG. 1B) consistent with the sagittal lumbar lordosis angle λB of FIG. 2B. In this manner, the vertebrae 116(1)-116(N1) may be immobilized relative to each other when the immobilization system 203 is fully implemented within the patient 102.

Other procedures may be performed as part of the immobilization, particularly when spinal nerves (not shown) are pinched or ligaments undesirably buckle in the vertebral canal by intervertebral disk degeneration. FIG. 2C is a partial lateral view of interbody cages 216A, 216B being implanted between adjacent vertebrae 116(2), 116(3) while the patient 102 is supported in a prone position. The interbody cage 216A, 216B may be implanted with the torque driver 204 while the vertebrae 116(2), 116(3) are positioned with the second angle λB (lambda_B) of a sagittal lumbar lordosis lordosis k (lambda) consistent with angle λ2 of FIG. 2B. The interbody cages 216A, 216B may include hollow bodies 218A, 218B filled with bone graft that assist in the process of the adjacent vertebrae 116(2), 116(3) to heal together firmly. The interbody cages 216A, 216B may be implanted within holes 220A, 220B that are drilled precisely between the adjacent vertebrae 116(2), 116(3) for precise placement of the interbody cages 216A, 216B. The interbody cages 216A, 216B may be implanted side by side to separate the vertebrae 116(2), 116(3) as outer threads 222A, 222B of the interbody cages 216A, 216B interface with the vertebrae 116(2), 116(3) to assist in locking the vertebrae 116(2), 116(3) in place. The interbody cages 216A, 216B help separate the vertebrae 116(2), 116(3) to decompress spinal nerves (not shown) that travel laterally outward from the vertebral canal and through openings called neural foramen (not shown) formed between adjacent ones of the vertebrae. The interbody cages 216A, 216B may include a strong rigid material, for example, metal, graphite, or bone to facilitate the separation of the vertebrae 116(2), 116(3). Without the interbody cages 216A, 216B providing the separation, these spinal nerves may be pinched and risk injury to the patient 102.

Further, the additional separation provided by the interbody cages 216A, 216B may also relieve pain by pulling more taut ligaments (not shown) to avoid ligament buckling that may also undesirably impinge nerves in the vertebral canal. Over time the interbody cages 216A, 216B may form a bone graft with the adjacent vertebrae 116(2), 116(3). The immobilization system 203 discussed earlier may rigidly secure the vertebrae 116(2), 116(3) together until the bone graft heals and the vertebrae 116(2), 116(3) are fused together with the second angle κB (lambda_B) of a sagittal lumbar lordosis lordosis λ (lambda). In this manner, the immobilization system 203 in combination with the interbody cages 216A, 216B may act cooperatively to reduce pain while the 116(1)-116(N1) are positioned with the desired sagittal lumbar lordosis λB using the lordosis adjustment subassembly 110.

Figures 2D, 2E, 2F:
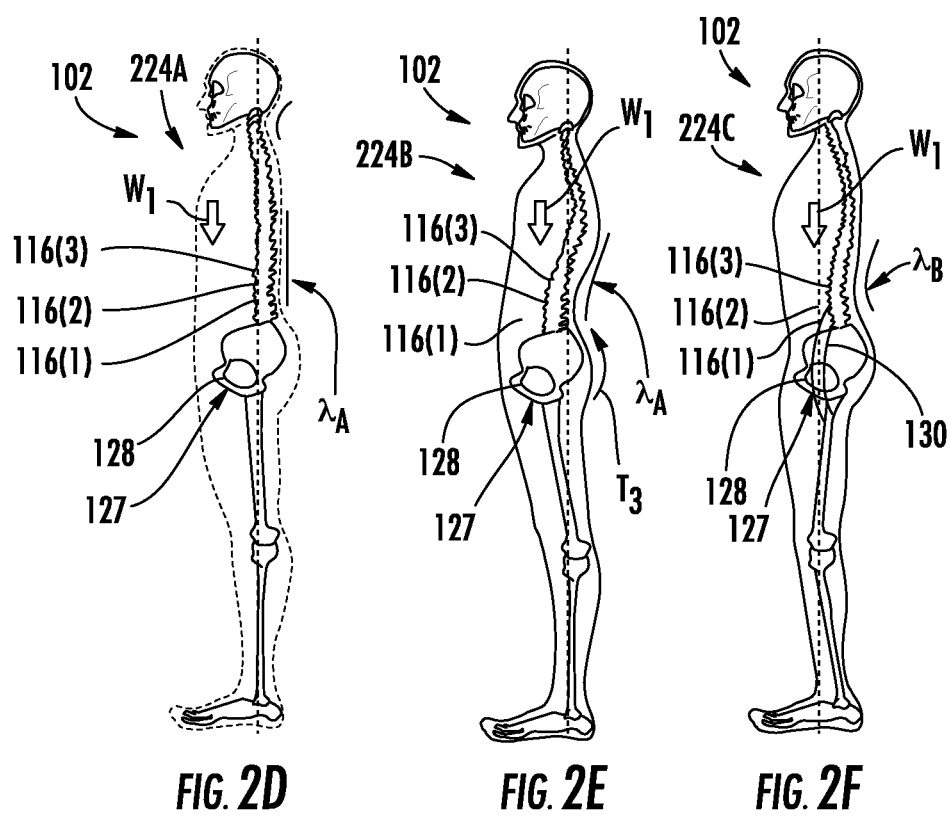
FIGS. 2D through 2F are left traverse views, respectively, of the patient exhibiting a flat back posture associated with a reduced angle of lordosis, a sway back posture compensating for the reduced angle of lordosis, and a desired spinal posture associated with a desired angle of lordosis.

Now that exemplary surgical procedures sensitive to the lordosis angle have been introduced, FIGS. 2D through 2F illustrate long term spinal profiles that may result from these surgical procedures. In this regard, FIGS. 2D through 2F are left traverse views, respectively, of the patient 102 exhibiting a flat back posture 224A associated with the vertebrae permanently arranged with a reduced lordosis angle λA, a sway back posture 224B compensating for the reduced lordosis angle λA, and a desired spinal posture 224C associated with a more desirable lordosis angle λB. The reduced lordosis angle λA may be temporarily desirable during surgery for insertion of the pedicle screws 200(1)-200(N2) when increased posterior separation of the vertebrae 116(1)-116(N1) is desirable, so that the pedicle screws 200(1)-200(N2) may be inserted efficiently and more precisely into various ones of the vertebrae 116(1)-116(N1). However, the reduced lordosis angle λA may not be a desirable arrangement of the vertebrae when permanently fusing the vertebrae together. Accordingly, the increased lordosis angle λB may be more desirable for procedures resulting in the permanent arrangement of the vertebrae, such as involving the connection of the immobilization rod 202 to the pedicle screws 200(1)-200(N2) and the implantation of the interbody cages 216A, 216B into the vertebral column.

Specifically, if the vertebrae 116(1)-116(N1) are permanently positioned in the reduced lordosis angle λA, then poor patient outcomes may result. These poor outcomes may occur if the connection of the immobilization rod 202 and/or implantation of the interbody cages 216A, 216B occur when the vertebrae are positioned with the reduced lordosis angle λA. With these other surgical procedures, the vertebrae becomes fixed with this reduced lordosis angle λA and the flat back profile 224A of FIG. 2D may result. The flat back posture 224A is suboptimal, because the fractional weight W1 of the patient 102 is disposed in a position to the front (anterior) of the pelvis 128 resulting in an inefficient walking gait to compensate for the fractional weight W1 not being disposed above (superior) to the pelvis 128.

FIG. 2E is a left traverse view of the sway back posture 224B of the patient 102 that is generated when the patient 102 compensates for the inefficient walking gait by positioning the fractional weight W1 using muscles (not shown) to a position more aligned to the pelvis 128. The compensation occurs by tilting T3 (FIG. 2E) the pelvis 128 forward and this tilting T3 may with time cause a strain-induced discomfort and pain to be experienced in the patient 102. In contrast to the flat back posture 224A (FIG. 2D) and sway back posture 224B (FIG. 2E), FIG. 2F is a left transverse view of a desired spinal posture 224C wherein the vertebrae 116(1)-116(N1) are permanently fused during surgery with the desired lordosis angle λB that causes the fractional weight W1 to be disposed more in alignment with the pelvis 200 without additional muscular burden needed in the sway back posture 224B. Thus, strain-induced discomfort and stress associated with the sway back posture 224B may be avoided by optimizing the angle of lordosis of the vertebrae 116(1)-116(N1) for various procedures during spinal surgery using the lordosis adjustment subassembly 110.

Figure 3A:
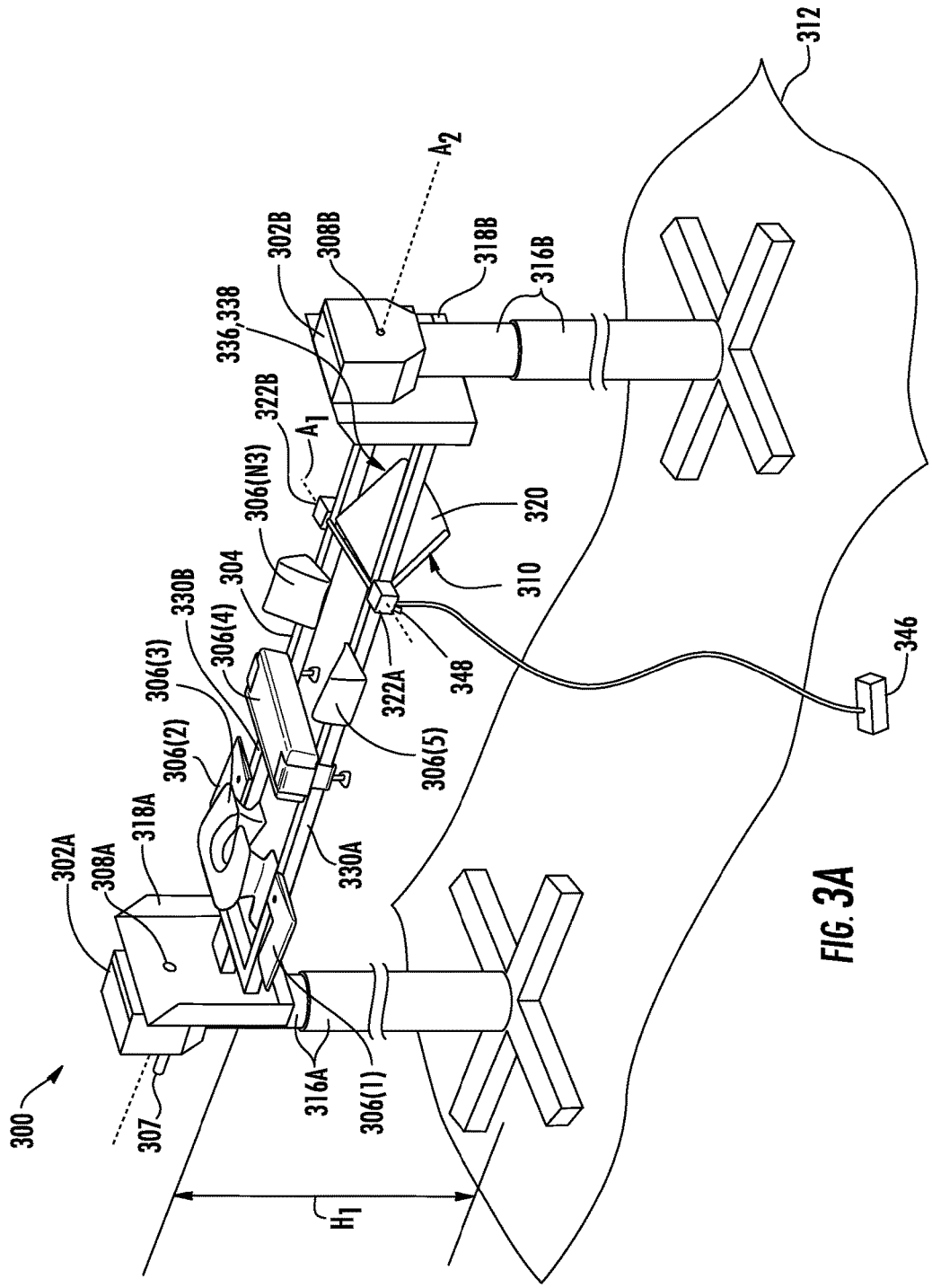
FIG. 3A is a top perspective view of an exemplary surgical table, which is a second embodiment of the surgical table of FIG. 1A, the second embodiment including includes a plurality of piers, a rigid frame rotatably coupled to the plurality of piers, at least one body pad, and an exemplary lordosis adjustment subassembly.
Figure 3B:
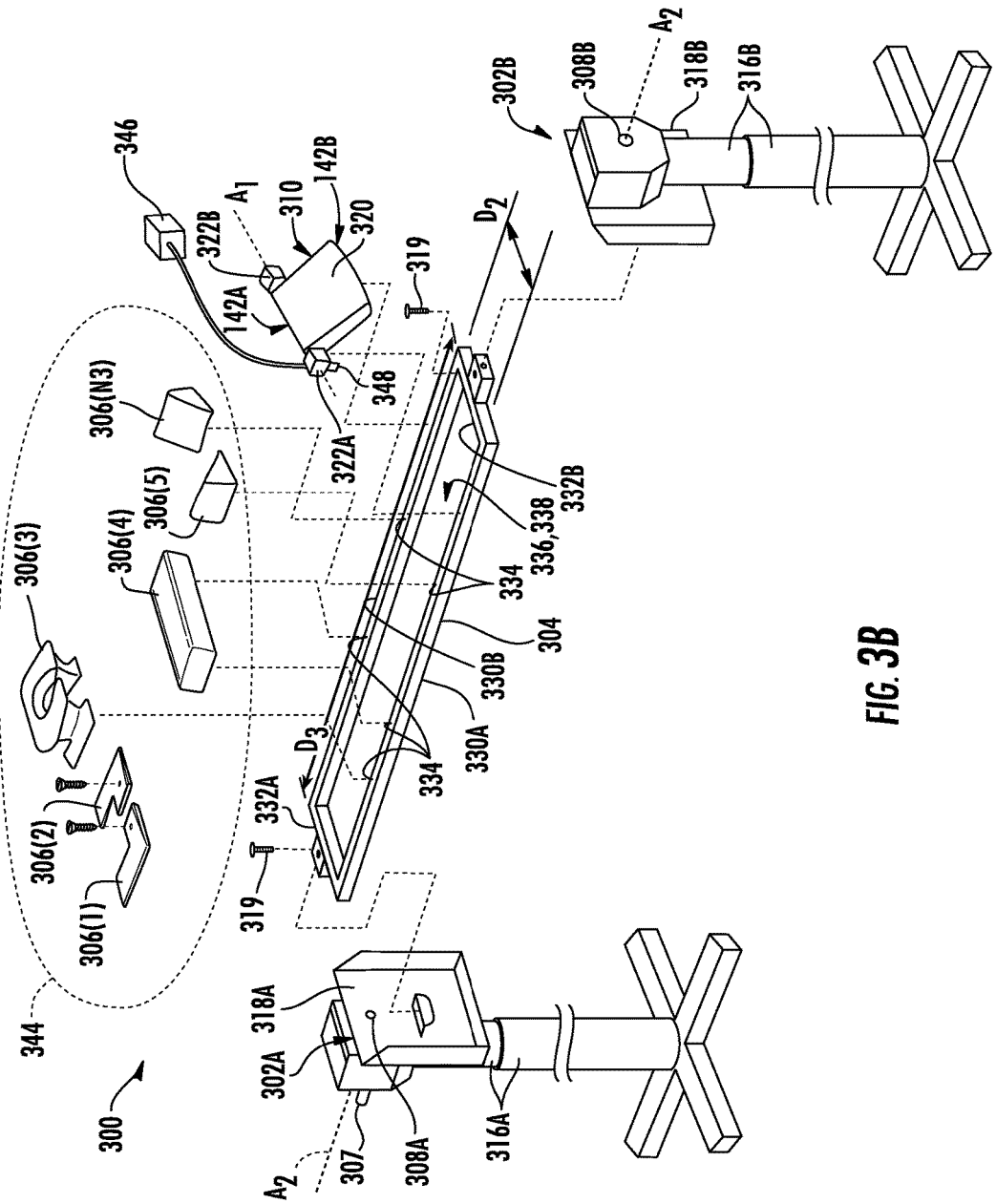
FIG. 3B is a top perspective and partially exploded view of the surgical table of FIG. 3A.

There are other embodiments of the surgical table 100 to optimize the lordosis angle during surgical procedures performed during spinal surgery. In this regard, FIG. 3A is a top perspective view of an exemplary surgical table 300, which is a second embodiment of the surgical table 100 of FIG. 1A. The surgical table 300 includes a plurality of piers 302A, 302B, a rigid frame 304, at least one body pad 306(1)-306(N3), and a lordosis adjustment subassembly 310. Also, FIG. 3B is a top perspective and partially exploded view of the surgical table 300 of FIG. 3A showing these components detached. Each of these components will now be discussed sequentially in detail.

In this regard, the plurality of piers 302A, 302B of the surgical table 300 operate to position and support the rigid frame 304 at a height H1 above a surgical floor 312. As discussed in more detail later, the rigid frame 304 supports the patient 102 in a prone position 314A during spinal surgery. The plurality of piers 302A, 302B respectively include structural portions 316A, 316B and frame receiving interfaces 318A, 318B. Each of the structural portions 316A, 316B extends from the surgical floor 312 to support the frame receiving interfaces 318A, 318B where the rigid frame 304 may be coupled. For example, fasteners 319 (FIG. 3B) may couple the frame receiving interfaces 318A, 318B to the rigid frame 304. In some embodiments, the piers 302A, 302B may be connected together (not shown) independently of the rigid frame 304 and for additional structural strength the piers 302A, 302B may also have telescoping capability to adjust the height H1 of the rigid frame 304 and the piers 302A, 302B may include casters or wheels (not shown) to abut against the surgical floor 312 and enable the surgical table 300 to be conveniently moved with the patient 102. In this manner, the piers 302A, 302B position the rigid frame 304 relative to the surgical floor 112.

Moreover, the frame receiving interfaces 318A, 318B of the piers 302A, 302B may be removably secured to the rigid frame 304, for example with the fasteners 319, so that the rigid frame 304 may be supported by the piers 302A, 302B through the frame receiving interfaces 318A, 318B. The frame receiving interfaces 318A, 318B may be supported by pier bearings 308A, 308B of the piers 302A, 302B. These pier bearings 308A, 308B in combination with an actuator 307 enable rotation of the rigid frame 304 about an axis of rotation A2 to facilitate angular positioning of the patient 102 in a range from a supine position 314B to a prone position 314A. In one non-limiting embodiment, the pier bearings 308A, 308B may include a roller bearing and the actuator 307 may be powered by electrical, mechanical, and/or manual means. In this manner, the piers 302A, 302B may position the rigid frame 304 supporting the patient 102.

With continued reference to FIGS. 3A and 3B, the rigid frame 304 of the surgical table 300 support components 344 of the surgical table 300 which directly abut against the patient 102, and the rigid frame 304 transfers the weight of the patient 102 to the frame receiving interfaces 318A, 318B. The rigid frame 304 may include strong and rigid materials (i.e., metal, aluminum, plastics, and/or composites) to support the weight of the patient 102 in a static position to avoid unnecessary movement of the patient 102 during spinal surgery. The rigid frame 304 may include first and second elongated portions 330A, 330B spaced apart and connected by a plurality of traverse elements 332A, 332B of which one or more may include fastener interfaces, for example, through-holes and/or threaded holes 334 (FIG. 3B) to facilitate the mounting of the components 344 and the lordosis adjustment subassembly 310 that may transfer the weight of the patient 102 to the rigid frame 304. The first and second elongated portions 330A, 330B and the traverse elements 332A, 332B may be formed integrally or secured together, for example, with fasteners (not shown) to provide a rigid body to resist the unnecessary movement of the patient 102 during surgery. The first and the second elongated portions 330A, 330B and the traverse elements 332A, 332B may surround an inner space 336 within which, as discussed later, a distal end 142B of the leg pad 320 of the lordosis support subassembly 310 may pass through. The inner space 336 as illustrated in FIG. 3B may include a rectangular or substantially rectangular shape 338 to provide strength by minimizing stress areas that may be included as part of alternative shapes (e.g., closed polygon shapes). Further, the first and the second elongated portions 330A, 330B may be separated by a distance D2 (FIG. 3B) to enable thighs 122 of the patient 102 to pass through the inner space 336 when supported by the leg pad 320. The distance D2 may be at least eleven (11) inches to be compatible with the thighs 122 of most patients 102. The length D3 of the rigid frame 304 may be configured to be approximately the length of the patient 102 to fully support the entire patient 102. Consistent with this, the length D3 may be in a range from sixty-six (66) to seventy-eight (78) inches. In this manner, the rigid frame 304 may facilitate the transfer the weight of the patient 102 to the piers 302A, 302B and statically position the patient 102 to facilitate a more precise insertion of the pedicle screws 200(1)-200(N2) into the vertebrae.

The patient positioning components 344 (FIG. 3B) of the surgical table 300 may transfer, to the rigid frame 304, the fractional weight W1 from the portion 124 of the patient 102 (FIG. 1A) of the patient 102 superior to the hip joint 127. These patient positioning components 344 include, for example, the body pads 306(1)-306(N3). The body pads 306(1)-306(N3) may be removably secured to the rigid frame 304, for example, with fasteners to customize the surgical table 300 for use with patients 102 of various sizes and treatment needs. The patient positioning components 344 may also include materials, for example foam cushioning, to prevent bruising of the patient 102 during spinal surgery. In this manner, the patient positioning components 344 may be used to position the patient relative to the rigid frame 304 of the surgical table to prevent injury to the patient 102.

With continued reference to FIGS. 3A and 3B, the lordosis adjustment subassembly 310 of the surgical table 300 enables sagittal lumbar lordosis between adjacent ones of the vertebrae 116(1)-116(N1) to be optimized during spinal surgery. The lordosis adjustment subassembly 310 may be a second embodiment of the lumbar lordosis subassembly 110 (FIG. 1A). The lordosis adjustment subassembly 310 includes the leg pad 320 and at least one hinge portion 322A, 322B. The leg pad 320 may be configured to support and position the thighs 122 of the patient 102 during spinal surgery when the patient 102 is in the prone position. The leg pad 320 may be attached to the rigid frame 304 with the hinge portion 322 to enable the leg pad 320 of the lordosis adjustment subassembly 310 to pivot about an axis of rotation A1. The hinge portion 322 may include an actuator 348 with a user interface 346 to selectively control the angular subsystem position Φ (phi) of the lordosis adjustment subassembly 310. The actuator 348 may be powered by various means, for example, manual, electric, electro-mechanical, and/or hydraulic means. The angular subsystem position Φ (phi) may be in a range, for example, from zero (0) to one-hundred thirty five (135) degrees to enable the attending surgeon to implement a desired lumbar lordosis.

Figure 4A:
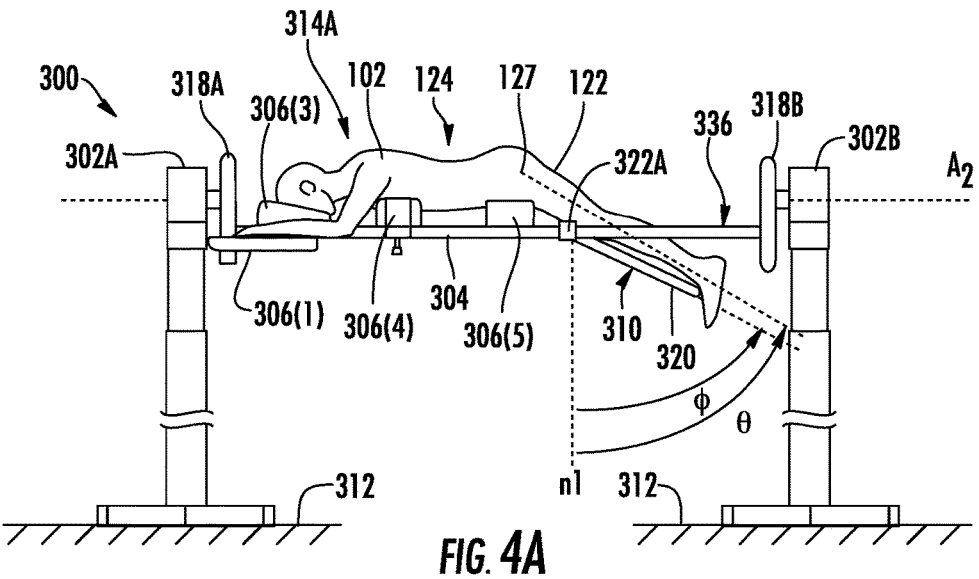
FIGS. 4A through 4C are a right side view, top view, and front view, respectively, of a patient supported in the prone position by the surgical table of FIG. 3A during spinal surgery.
Figure 4B:
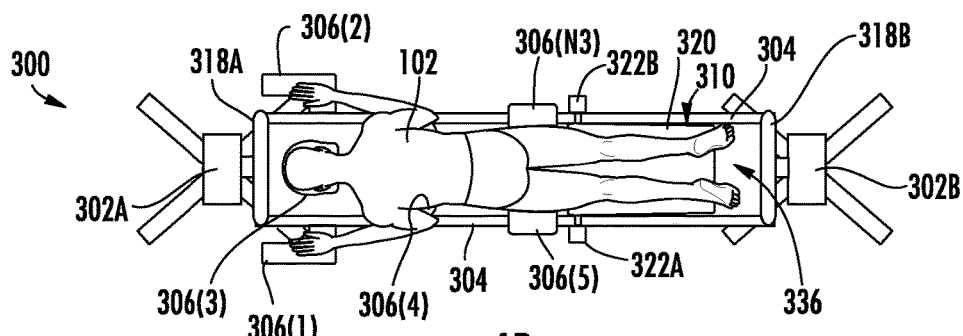
Figure 4C:
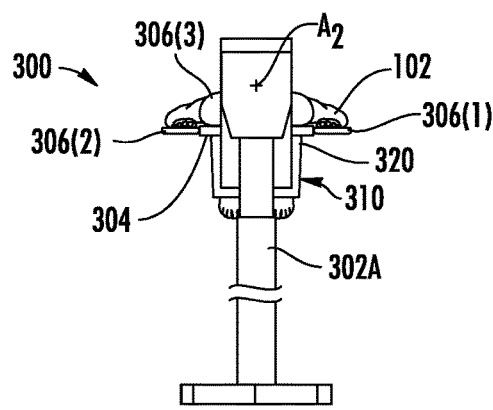

The angular subsystem position Φ (phi) of the leg pad 320 may be used to optimize lumbar lordosis of the vertebrae 116(1)-116(N1) during insertion of the pedicle screws 200 (1)-200(N2) into various ones of the vertebrae 116(1)-116 (N1) and connection of the immobilization rod 202. FIGS. 4A through 4C are a right side view, top view, and front view, respectively, of the surgical table of FIG. 3A with the patient 102 in the prone position during spinal surgery. The leg pad 320 is pivoted about the axis of rotation A1 to the angular subassembly position Φ (phi) relative to a normal n1 of the rigid frame 304 while the thighs 122 of the patient 102 are at least supported by the leg pad 320 and rotate to an angular thigh position θ (theta) about the hip joints 127. The weight of the thighs 122 of the patient 102 may keep the thighs 122 in contact with the leg pad 320, and it is contemplated that in some embodiments that the thighs 122 may also be secured to the leg pad 320 with straps (not shown) extending from the leg pad 320 and surrounding the thighs 122. Accordingly, as the leg pad 320 moves to different ones of the angular subassembly position Φ (phi), then the angular thigh position θ (theta) is determined as the patient positioning components 344 keep the portion 124 of the patient 102 in a static relationship relative to the rigid frame 304 during spinal surgery.

FIG. 5A is a right side view of the surgical table 300 of FIG. 3A supporting the patient 102 with the leg pad 320 of the lordosis adjustment subassembly 310 moved to an exemplary angular subassembly position $\Phi_1$ (phi_1) with respect to the rigid frame 304 resulting in the thighs 122 of the patient 102 to be positioned at an exemplary angular thigh position θ1 (theta_1) relative to an superior body portion 124 of the patient 102. FIG. 5B is a graph showing the relationship of the angular thigh position θ (theta) of FIG. 5A to a respective lumbar lordosis angle. The relationship shows that increasing the angular thigh position θ (theta) is associated with higher angles of lumbar lordosis due to the internal structures of the patient 102, for example, the psoas muscle 130 (FIG. 1A) which connects the thighs 122 of the patient 102 to various ones of the vertebrae 116(1)-116(N1) and urges these vertebrae into an increasing lumbar lordosis orientation as the angular thigh position θ (theta) is increased. The lumbar lordosis λA (lambda_A) and lumbar lordosis λB (lambda_B) indicate exemplary desired angles of lumbar lordosis for inserting (FIG. 2A) the pedicle screws 200(1)-200(N2) and connecting (FIG. 2B) the immobilization rod 202, respectively. As depicted in FIG. 5B, the angle of the lumbar lordosis λ1 (lambda_1) is within the acceptable range of the lumbar lordosis λA (lambda_A) for insertion of the pedicle screws 200(1)-200(N2) into various ones of the vertebrae 116(1)-116(N1). In this manner, the pedicle screws may be inserted with precision.

FIG. 6A is a right side view of the surgical table 300 of FIG. 3A supporting the patient 102 with the leg pad 320 of the lordosis adjustment subassembly 310 moved to an exemplary angular subassembly position $\Phi_X$ (phi_X) with respect to the rigid frame 304 resulting in the thighs 122 of the patient 102 to be positioned at an exemplary angular thigh position $\theta_X$ (theta_X) relative to the superior body portion 124 of the patient 102. FIG. 6B is a graph showing the relationship of the angular thigh position θ (theta) of FIG. 6A to a respective second lumbar lordosis angle. As depicted in FIG. 6B, the angle of the lumbar lordosis λX (lambda_X) is between the acceptable range of the lumbar lordosis λA (lambda_A) and the acceptable range of the lumbar lordosis λB (lambda_B) for connecting the immobilization rod 202 to the pedicle screws 200(1)-200(N2). Accordingly, the lumbar lordosis at this angular subassembly position $\Phi_X$ (phi_X) is not optimal for inserting the pedicle screws or connecting the immobilization rod 202. The attending physician may observe and diagnose this conclusion. In this sub-optimal situation the angular subassembly position $\Phi_X$ (phi_X) may be modified for the surgical procedure.

FIG. 7A is a right side view of the surgical table 300 of FIG. 3A supporting the patient 102 with the leg pad 320 of the lordosis adjustment subassembly 310 moved to an exemplary angular subassembly position $\Phi_2$ (phi_2) with respect to the rigid frame 304 resulting in the thighs 122 of the patient 102 to be positioned at an exemplary angular thigh position θ2 (theta_2) relative to the superior body portion 124 of the patient 102. FIG. 7B is a graph showing the relationship of the angular thigh position θ (theta) of FIG. 7A to a respective lumbar lordosis characteristic of the adjacent vertebrae of the patient 102. As depicted in FIG. 7B, the angle of the lumbar lordosis λ3 (lambda_3) is within the acceptable range of the lumbar lordosis λB (lambda_B) as desired for connecting the immobilization rod 202 to the pedicle screws 200(1)-200(N2). In this manner, the immobilization rod 202 may be connected to fuse various ones of the vertebrae together with the desired sagittal lumbar lordosis to provide long-term improved posture and associated comfort to the patient 102.

Now that the surgical table 300 has been introduced, additional details of the lordosis adjustment subassembly 310 are now provided. FIGS. 8A through 8D are a bottom perspective view, bottom perspective exploded view, bottom view, and front view, respectively, of the lordosis adjustment subassembly 310 of FIG. 3A. In this regard, the lordosis adjustment subassembly 310 may include the leg pad 320, the hinge portions 322A, 322B, the actuator 348, and the user interface 346. The thighs 122 (FIG. 4A) of the patient 102 may be supported by the leg pad 320, and the portion 124 of the patient 102 superior to the hip joint 127 (FIG. 4A) supported statically relative to the rigid frame 304. The leg pad 320 is connected to the rigid frame 304 with the hinge portions 322A, 322B and may be rotated relative to the rigid frame 304 according to the user interface 346 coupled to the actuator 348 of the hinge portion 322A. In one non-limiting embodiment, the actuator 348 may angularly move the leg pad 320 by being angularly coupled to an axle 347 of the lordosis adjustment subassembly 310 through a plurality of gears 349A, 349B. The first gear 349A may be directly driven by the actuator 348 and another gear 349B may be directly coupled to the axle 347. In this manner, the thighs 122 of the patient may be rotated while the portion 124 of the patient 102 superior to the hip joint 127 remains supported statically by the body pads 306(1)-306(N3) during spinal surgery. Providing this angular rotation of the thighs 122 facilitates control of the sagittal lumbar lordosis as discussed earlier.

Figure 9:
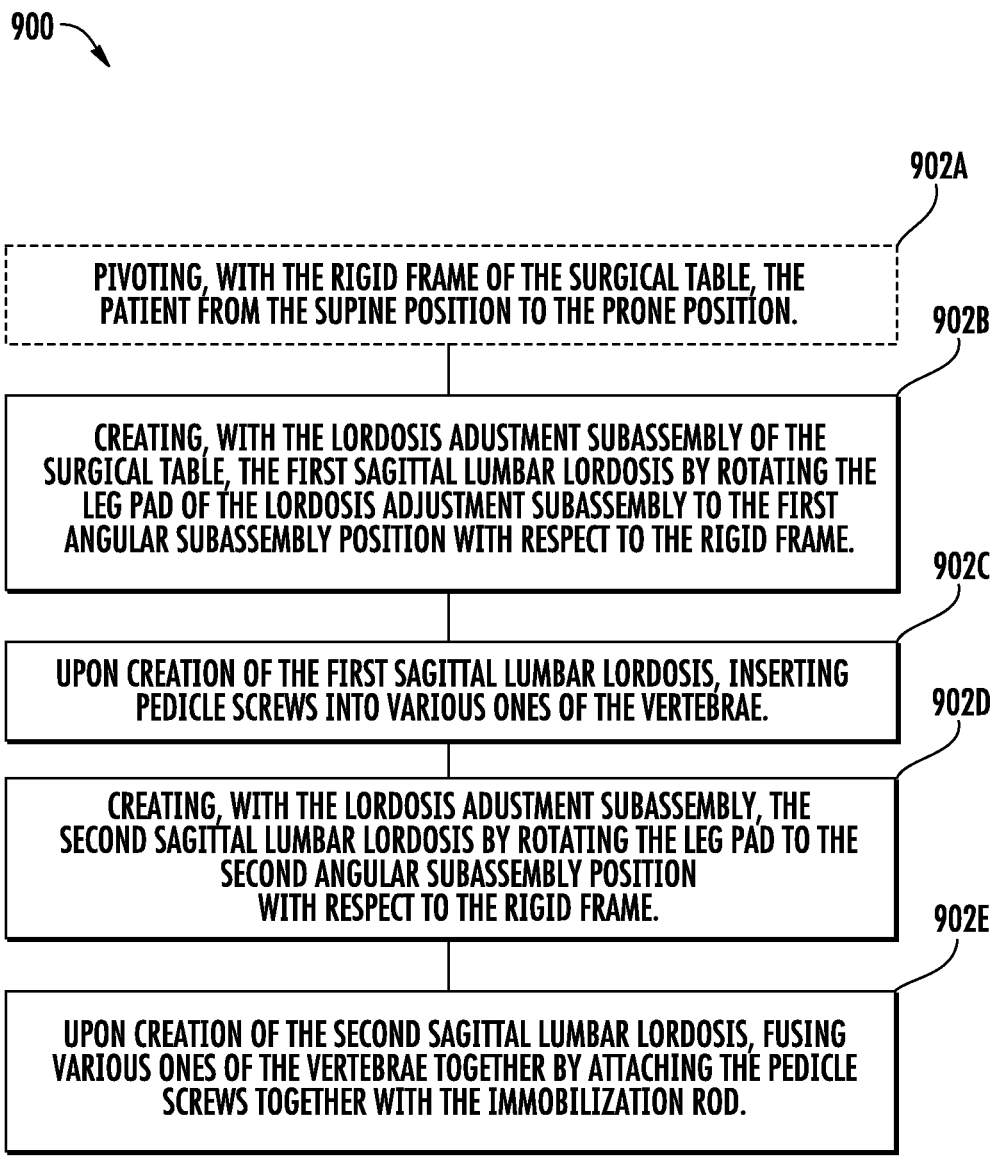
FIG. 9 is a flowchart of an exemplary method for fusing adjacent vertebrae during spinal surgery with the surgical table of FIG. 3A.

FIG. 9 is a flowchart of an exemplary method 900 for fusing various ones of the vertebrae 116(1)-116(N1) together during spinal surgery with the surgical table 300 of FIG. 3A. The method 900 is now discussed using the terminology discussed above and below in relation to the operations 902A through 902E as depicted in FIG. 9. In this manner, the attending physician may conveniently select optimal amounts of lumbar lordosis at various ones of the vertebrae 116(1)-116(N1) consistent with of the insertion of the pedicle screws 200(1)-200(N2) and connection of the immobilization rod 202 when limiting relative movement of the adjacent vertebrae 116(2), 116(N2) during spinal surgery.

Figure 10A:
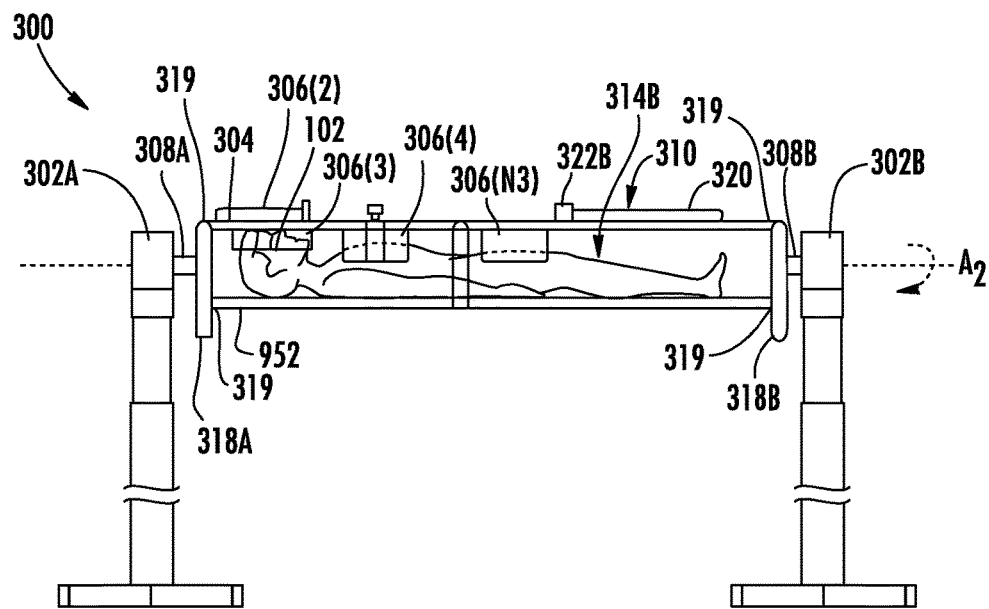
FIGS. 10A and 10B are right side views of the patient being supported in supine and prone positions, respectively, by the surgical table of FIG. 3A.
Figure 10B:
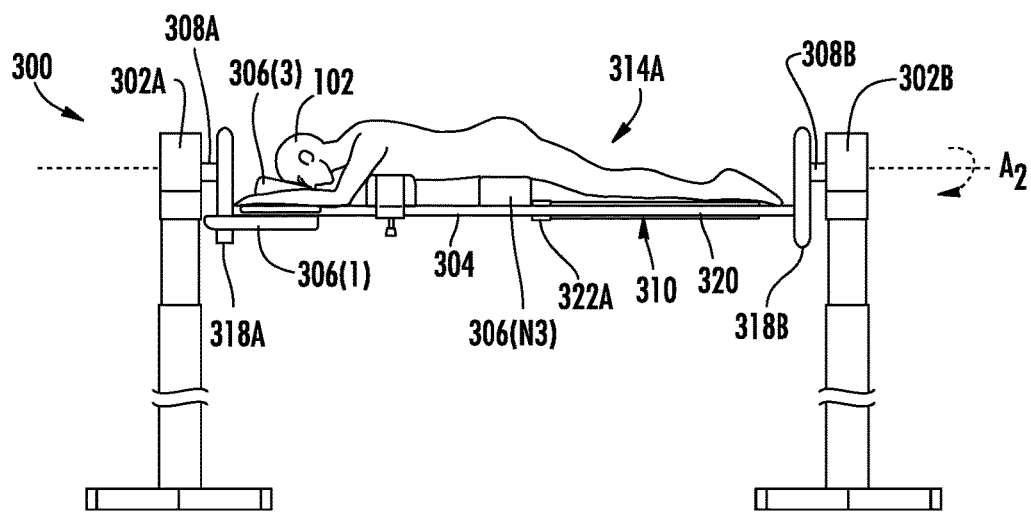

In order to position the patient 102 to begin the spinal surgery, the method 900 may include pivoting, with the rigid frame 304 of the surgical table 300, the patient 102 from a supine position 314B to a prone position 314A (operation 902A of FIG. 9). In this regard, FIGS. 10A and 10B are right side views of the patient 102 being supported in a supine position 314B and the prone position 314A, respectively, by the surgical table 300 of FIG. 3A. In FIG. 10A the patient 102 is supported in the surgical table 300 with a supine platform 952 removably attached to the frame receiving interfaces 318A, 318B of the surgical table 300 with fasteners (not shown) similar to the attachment approach discussed easier for the rigid frame 304. The supine platform 952 supports the patient 102 in the supine position 314B with the posterior of the patient 102 facing the supine platform 952 for convenience when moving the patient 102 to the surgical table 300. Upon the patient 102 being supported by the supine platform 952, the rigid frame 304 may be removably attached to the receiving interfaces 318A, 318B with fasteners 319 when the lordosis attachment subassembly 310 and the body pads 306(1)-306(N3) are secured to the rigid frame 304. The rigid frame 304 and the supine platform 952 with the patient 102 sandwiched inbetween is then pivoted about the axis of rotation A2 of the surgical table 30 until the patient 102 is disposed in the prone position. The axis of rotation A2 may be formed by the pier bearings 308A, 308B of the receiving interfaces 318A, 318B which rotate relative to the piers 302A, 302B. Once the patient 102 is in the prone position 314A, then the supine platform 952 is then detached from the receiving interfaces 318A, 318B as shown in FIG. 10B. In this manner, the patient 102 may be prepared for spinal surgery.

The method 900 may also include creating, with a lordosis adjustment subassembly 310 of the surgical table 300, the first sagittal lumbar lordosis λA (lambda_A) by moving the leg pad 320 to a first angular subassembly position $\Phi_1$ (phi_1) with respect to the rigid frame 304 (operation 902B of FIG. 9). The method 900 may also include upon creation of the first sagittal lumbar lordosis λA (lambda_A), inserting pedicle screws 200(1)-200(N2) into various ones of the vertebrae 116(1)-116(N1) (operation 902C of FIG. 9). In this manner, the pedicle screws 200(1)-200(N2) are inserted.

The method 900 may also include creating, with the lordosis adjustment subassembly 310, the second lumbar lordosis λB (lambda_B) between various ones of the vertebrae 116(1)-116(N1) of the patient 102 by moving the leg pad 320 to a second angular subassembly position $\Phi_2$ (phi_2) with respect to the rigid frame 304 (operation 902D of FIG. 9). The method 900 may also include upon creation of the second sagittal lumbar lordosis λB (lambda_A), fusing various ones of the vertebrae 116(1)-116(N1) together by attaching the pedicle screws 200(1)-200(N2) together with the immobilization rod 202 (operation 902E of FIG. 9). In this manner, various ones of the adjacent vertebrae 116(1)-116(N1) may be fused together using the surgical table 300.

Figure 11:
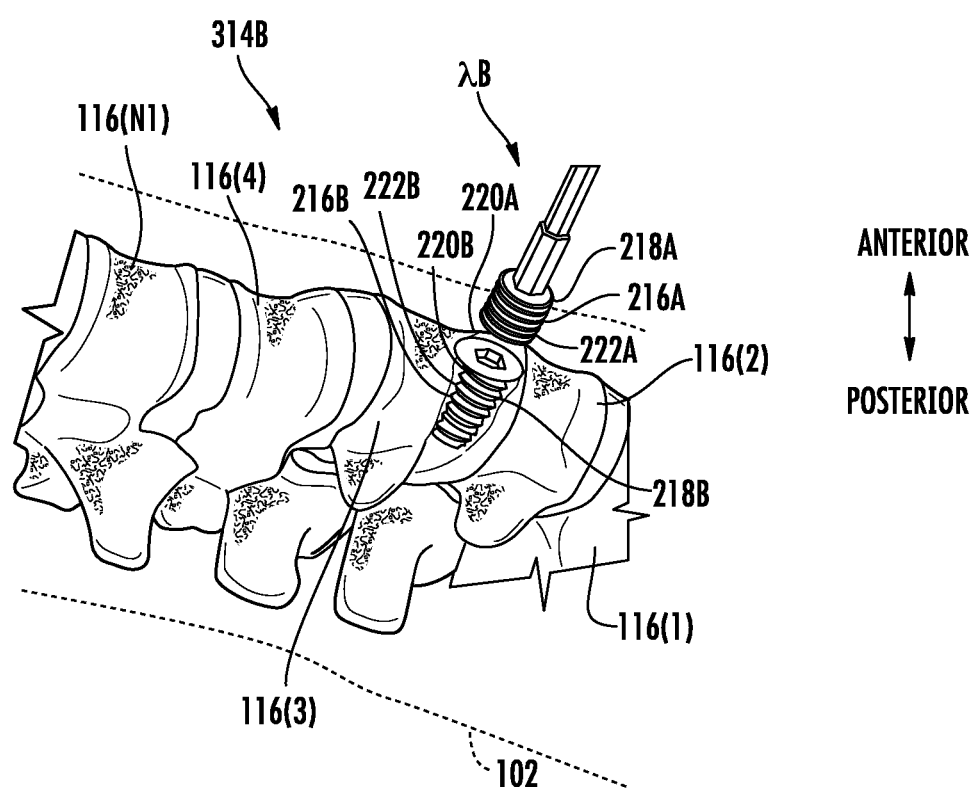
FIG. 11 is a partial lateral view of exemplary interbody cages being implanted between adjacent ones of the vertebrae of the patient in the supine position.

Not all of the procedures performed on the vertebrae 116(1)-116(N1) may occur while the patient 102 is positioned in the prone position 314A. In one example, FIG. 11 is a partial lateral view of the interbody cages 216A, 216B being implanted between various ones of the vertebrae 116(1)-116(N1) of the patient 102 in the supine position 314B when an abdomen (not shown) of the patient 102 may be more conveniently presented. In this situation, the interbody cages 216A, 216B may be implanted through at least one surgical opening (not shown). In these examples discussed above, procedures may be performed on various ones of the vertebrae 116(1)-116(N1) in one or more of the supine position 314B and the prone position 314A.

Many modifications and other embodiments not set forth herein will come to mind to one skilled in the art to which the embodiments pertain having the benefit of the teachings presented in the foregoing descriptions and the associated drawings. Therefore, it is to be understood that the description and claims are not to be limited to the specific embodiments disclosed and that modifications and other embodiments are intended to be included within the scope of the appended claims. It is intended that the embodiments cover the modifications and variations of the embodiments provided they come within the scope of the appended claims and their equivalents. Although specific terms are employed herein, they are used in a generic and descriptive sense only and not for purposes of limitation.

What is claimed is:

1. A surgical table for supporting a patient during spinal surgery, the surgical table comprising:
   a rigid frame including
      a plurality of traverse elements, and
      first and second elongated portions spaced apart by an inner space and connected by the plurality of traverse elements, wherein the first and the second elongated portions and the plurality of traverse elements define a perimeter of the inner space, and the inner space forming a passageway through the rigid frame;
   at least one body pad connected to the rigid frame and configured to transfer a weight of a portion of the patient to the rigid frame during the spinal surgery, wherein the portion is configured to be superior to a hip joint of the patient;
   a plurality of piers coupled with the rigid frame, the plurality of piers including pier bearings to position the rigid frame relative to a surgical floor, wherein the pier bearings are configured to rotate the rigid frame at least one-hundred eighty (180) degrees; and
   a lordosis adjustment subassembly including a leg pad and a hinge portion, wherein the leg pad is coupled to the rigid frame with the hinge portion, the hinge portion defining a range of motion of a distal end of the leg pad through the rigid frame,
   wherein the leg pad is configured to move independently of the rigid frame.

2. The surgical table of claim 1, wherein the first and the second elongated portions and the plurality of traverse elements are arranged to define a closed polygon shape.

3. The surgical table of claim 2, wherein the closed polygon shape includes a rectangular or substantially rectangular shape.

4. The surgical table of claim 1, wherein the first and the second elongated portions are spaced apart by at least eleven (11) inches.

5. The surgical table of claim 1, wherein the lordosis adjustment subassembly includes an actuator configured to change an angular subassembly position of the leg pad relative to the rigid frame.

6. The surgical table of claim 5, wherein the actuator comprises an electric motor.

7. The surgical table of claim 1, wherein the hinge portion defines an axis of rotation for the leg pad, wherein the axis of rotation is disposed outside the inner space.

8. The surgical table of claim 1, wherein a length of the rigid frame is in a range from sixty-six to seventy-eight inches.

9. The surgical table of claim 1,
   wherein the lordosis adjustment subassembly includes an axle secured to the leg pad,
   wherein the hinge portion is coupled to the leg pad through the axle, and the axle defines an axis of rotation enabling the distal end of the leg pad to rotate about the hinge portion.

10. The surgical table of claim 9, wherein the axis of rotation has a range of at least one-hundred thirty-five (135) degrees.

11. The surgical table of claim 9, further comprises an actuator configured to change an angular subassembly position of the leg pad relative to the hinge portion.

12. The surgical table of claim 11, wherein the actuator comprises an electric motor.

13. The surgical table of claim 11, further comprising a plurality of gears angularly coupled to the actuator and the axle.

14. The surgical table of claim 11, further comprises a locking system to reversibly hold constant the angular subassembly position of the leg pad relative to the hinge portion.

15. The surgical table of claim 14, wherein the locking system includes a cotter pin to form a mechanical interference between the hinge portion and the axle.

16. A method of making a surgical table for spinal surgery, comprising:
   connecting, with a plurality of traverse elements of a rigid frame of the surgical table, first and second elongated portions of the rigid frame that are spaced apart by an inner space, wherein the first and the second elongated portions and the plurality of traverse elements define a perimeter of the inner space, and the inner space forming a passageway through the rigid frame;
   connecting at least one body pad to the rigid frame, wherein the at least one body pad is configured to transfer a weight of a portion of a patient to the rigid frame during spinal surgery, wherein the portion is configured to be superior to a hip joint of the patient;
   coupling a plurality of piers with the rigid frame, the plurality of piers including pier bearings to position the rigid frame relative to a surgical floor, wherein the pier bearings are configured to rotate the rigid frame at least one-hundred eighty (180) degrees; and
   coupling a leg pad of a lordosis adjustment subassembly to the rigid frame with a hinge portion,
   wherein the hinge portion defines a range of motion of a distal end of the leg pad through the rigid frame and the leg pad is configured to move independently of the rigid frame.

17. The method of claim 16, further comprising changing, with an actuator of the lordosis adjustment subassembly, an angular subassembly position of the leg pad relative to the rigid frame and within the range of motion.

18. The method of claim 17, wherein the changing of the angular subassembly position is at least one-hundred thirty-five (135) degrees.

* * * * *